(12) United States Patent
Kanazaki et al.

(10) Patent No.: US 10,743,770 B2
(45) Date of Patent: Aug. 18, 2020

(54) PHOTOACOUSTIC DEVICE

(71) Applicant: CANON KABUSHIKI KAISHA, Tokyo (JP)

(72) Inventors: Kengo Kanazaki, Yokohama (JP); Tatsuki Fukui, Yokohama (JP); Satoshi Yuasa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 435 days.

(21) Appl. No.: 15/158,719

(22) Filed: May 19, 2016

(65) Prior Publication Data
US 2016/0345838 A1 Dec. 1, 2016

(30) Foreign Application Priority Data

May 26, 2015 (JP) .................................. 2015-106577

(51) Int. Cl.
A61B 5/00 (2006.01)
A61B 5/145 (2006.01)

(52) U.S. Cl.
CPC ........ *A61B 5/0095* (2013.01); *A61B 5/14542* (2013.01); *A61B 5/7203* (2013.01); *A61B 5/14546* (2013.01)

(58) Field of Classification Search
CPC . A61B 5/0095; A61B 5/7203; A61B 5/14542; A61B 5/14546
USPC .................................................. 600/437–480
See application file for complete search history.

(56) References Cited

U.S. PATENT DOCUMENTS

| 8,652,441 | B2 | 2/2014 | Fukui et al. ................... 424/9.6 |
| 9,743,881 | B2* | 8/2017 | Radulescu ........... A61B 5/0044 |
| 9,949,717 | B2* | 4/2018 | Rozental ................ G01H 9/004 |
| 2008/0221647 | A1* | 9/2008 | Chamberland ...... A61B 5/0095 607/88 |
| 2009/0002685 | A1* | 1/2009 | Fukutani .............. A61B 5/0073 356/72 |
| 2011/0117023 | A1 | 5/2011 | Yamauchi et al. ............. 424/9.1 |
| 2012/0027679 | A1 | 2/2012 | Yamauchi et al. ............. 424/9.1 |
| 2013/0199299 | A1* | 8/2013 | Wang ................... A61B 5/0095 73/655 |
| 2014/0023584 | A1 | 1/2014 | Yamauchi et al. ........... 424/1.49 |

(Continued)

OTHER PUBLICATIONS

G.R. Cherrick et al., "Indocyanine Green: Observations on Its Physical Properties, Plasma Decay, and Hepatic Extraction", *J Clin Invest.*, vol. 39, No. 4; pp. 592-600 (Apr. 1960).

(Continued)

Primary Examiner — Sanjay Cattungal
(74) Attorney, Agent, or Firm — Venable LLP

(57) ABSTRACT

A photoacoustic device comprises a light source configured to generate first and second lights; an irradiation unit configured to generate a first acoustic wave from an object including a contrast agent by irradiating the object with the first light, and then bleach the contrast agent by irradiating the object with the second light and generate a second acoustic wave from the object by irradiating the object with the first light after bleaching; a receiving unit configured to output a first signal upon receiving the first acoustic wave and output a second signal upon receiving the second acoustic wave; and an acquisition unit configured to acquire first information based on the first signal, and acquire second information based on the second signal.

22 Claims, 9 Drawing Sheets

(56) References Cited

U.S. PATENT DOCUMENTS

| | | | | |
|---|---|---|---|---|
| 2014/0046165 A1* | 2/2014 | Fukutani | .............. | A61B 5/0095 |
| | | | | 600/407 |
| 2014/0371571 A1* | 12/2014 | Tsujita | ................. | A61B 8/5215 |
| | | | | 600/407 |
| 2015/0245771 A1* | 9/2015 | Wang | ................... | A61B 5/0095 |
| | | | | 600/411 |
| 2015/0272444 A1* | 10/2015 | Maslov | ................ | A61B 5/0095 |
| | | | | 600/407 |
| 2017/0100039 A1* | 4/2017 | Fukutani | .............. | A61B 5/0095 |

OTHER PUBLICATIONS

E.M.S. Stennett et al., "Photophysical Processes in Single Molecule Organic Fluorescent Probes", *Chemical Society Reviews*, vol. 43, No. 4, pp. 1057-1075 (Feb. 21, 2014).

* cited by examiner

PHOTOACOUSTIC DEVICE

BACKGROUND OF THE INVENTION

Field of the Invention

The present invention relates to a photoacoustic device.

Description of the Related Art

The research of optical imaging devices in which a living body is irradiated with light from a light source such as a laser, and information on the inside of the living body which is obtained on the basis of the incident light is represented as an image has been actively advanced. Photoacoustic tomography (PAT) is one of such optical imaging techniques. In the photoacoustic tomography, a living body is irradiated with pulsed light generated from a light source, and a photoacoustic wave (typically, ultrasonic wave) generated from a living body tissue which has absorbed the energy of the pulsed light propagated and diffused inside the living body is detected. The obtained signals are subjected to mathematical analysis processing (image reconstruction processing) with an information processing device, and information relating to optical property values of the object interior is visualized. As a result, it is possible to obtain information on the object interior, for example, the initial sound pressure, optical property values (in particular, the light energy absorption density and absorption coefficient) and distributions thereof, and this information can be used for specifying the distribution of absorbents in the living body and locations of malignant tumors.

In PAT, the initial sound pressure P0 of the acoustic wave generated from a light absorbent inside an object can be represented by the following mathematical formula (I).

$$P0 = \Gamma \cdot \mu a \cdot \Phi \quad (I)$$

In this formula, $\Gamma$ is a Gruneisen parameter, which is obtained by dividing the product of the volume expansion coefficient $\beta$ and the square of the speed of sound c by the heat capacity Cp at constant pressure. $\Gamma$ is known to have a substantially constant value for the same object. Further, $\mu a$ is the absorption coefficient of a light absorber, and $\Phi$ is the quantity of light at the position of the light absorber (quantity of light by which the light absorber is irradiated; also referred to as "light fluence"). The initial sound pressure P0 generated by the light absorber inside the object propagates as an acoustic wave inside the object and is detected by an acoustic detector arranged on the object surface. Changes with time of the detected sound pressure of the acoustic wave are detected, and the initial sound pressure distribution P0 can be calculated from the measurement results by using an image reconstruction technique such as back projection. By dividing the calculated initial sound pressure distribution P0 by the Gruneisen parameter $\Gamma$, it is possible to obtain the distribution of the product of $\mu a$ and $\Phi$, that is, the light energy density distribution. Further, where the light quantity distribution $\Phi$ inside the object is known, the absorption coefficient distribution $\mu a$ can be obtained by dividing the light energy density distribution by the light quantity distribution $\Phi$. Thus, where an absorber having known optical properties with respect to the light by which the object is irradiated is introduced as a contrast agent, an ultrasound signal corresponding to the amount of the contrast agent present can be acquired.

Assuming that a living body is the object, blood (hemoglobin) is an absorber with a high degree of absorption of near-IR radiation. Thus, where measurements on a living body are performed by PAT using near-IR radiation, information relating to spatial distribution of blood can be obtained. However, when a sufficient signal contrast (S/N) cannot be obtained only with the amount of hemoglobin present, where a light absorber is further introduced as a contrast agent, it is possible to obtain a PAT image with the S/N enhanced according to the concentration at which the light absorber is present. Contrast agents for blood vessels, which can be used in a living body, are required to be safe with respect to the living body and to have optical properties enabling effective absorption of light in a wavelength region with a high transmissivity in the living body.

For example, Indocyanine Green (abbreviated hereinbelow as ICG) is a contrast agent for blood vessel imaging that demonstrates the above-described performance. Since ICG is a light absorber that produces little adverse effect when a human body is irradiated and that effectively absorbs light in a near-IR wavelength region where high transmissivity in a living body is demonstrated (Gilbert R. Cherrick, Samuel W. Stein, Carroll M. Leevy, Charles S. Davidson, "INDOCYANINE GREEN: OBSERVATIONS ON ITS PHYSICAL PROPERTIES, PLASMA DECAY, AND HEPATIC EXTRACTION", J Clin Invest., 1960 April; 39 (4): p. 592-600; referred to hereinbelow as Cherrick et al.), it can be advantageously used as a contrast agent in a PAT device.

In this respect, the problem which remains to be solved is that it is difficult to distinguish between an image signal component based on a photoacoustic wave from hemoglobin and an image signal component based on a photoacoustic wave from a contrast agent, and only information in which the two image signal components are mixed can be acquired.

With the foregoing in view, it is an objective of the present invention to provide a photoacoustic device that can acquire more accurate object information.

SUMMARY OF THE INVENTION

The present invention in its one aspect provides a photoacoustic device comprising a light source configured to generate first and second lights; an irradiation unit configured to generate a first acoustic wave from an object including a contrast agent by irradiating the object with the first light from the light source, and then bleach the contrast agent inside the object by irradiating the object including the contrast agent with the second light from the light source and generate a second acoustic wave from the object by irradiating the object with the first light from the light source after bleaching the contrast agent; a receiving unit configured to output a first electric signal upon receiving the first acoustic wave and output a second electric signal upon receiving the second acoustic wave; and an acquisition unit configured to acquire first property information on the object on the basis of the first electric signal, and acquire second property information on the object on the basis of the second electric signal.

Further features of the present invention will become apparent from the following description of exemplary embodiments with reference to the attached drawings.

DESCRIPTION OF THE EMBODIMENTS

Figure 1:
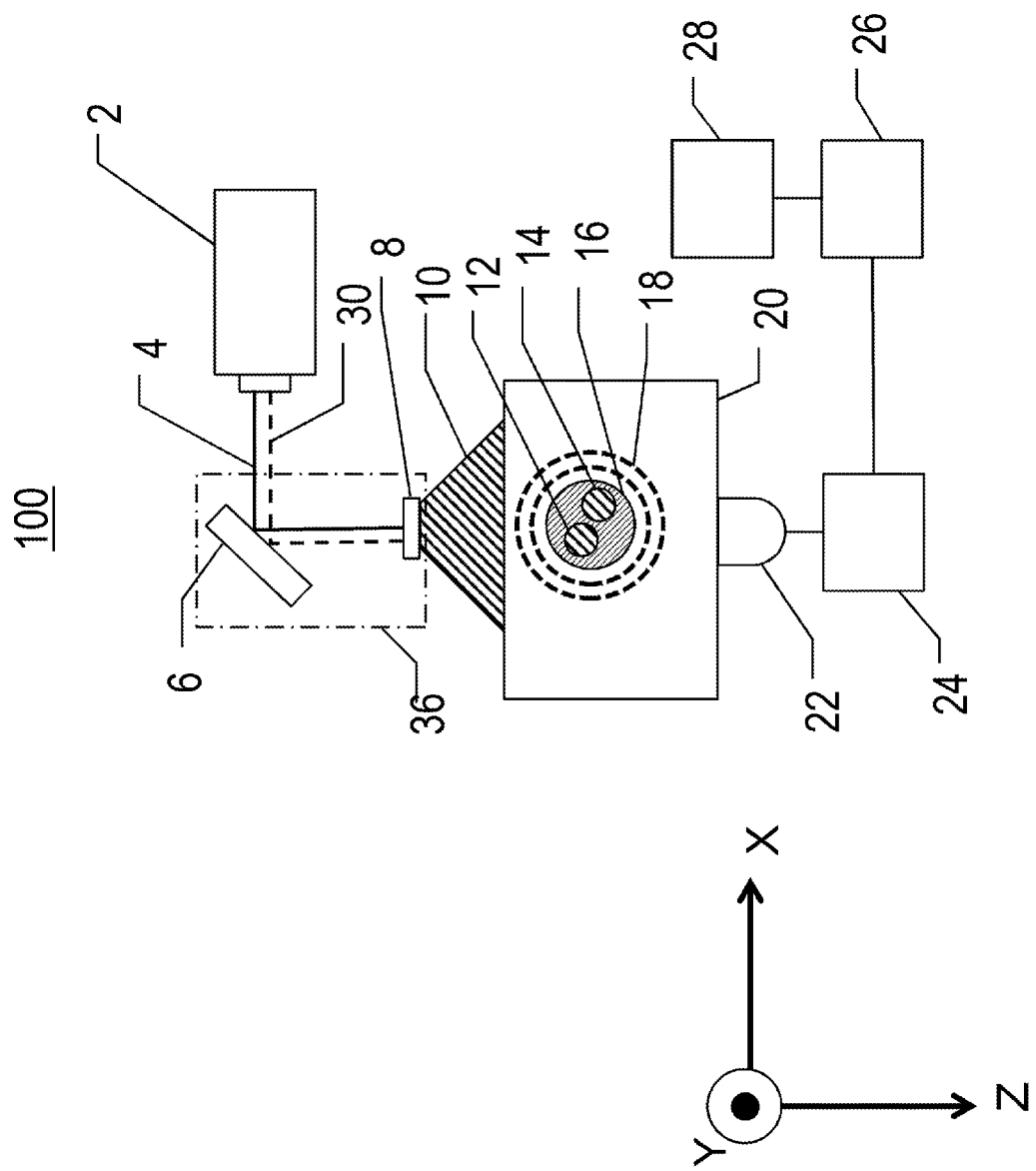
FIG. 1 is a block diagram illustrating Example 1 of the photoacoustic device of the present invention.

The embodiments of the present invention will be explained hereinbelow in greater detail with reference to the appended drawings. The same constituent elements are assigned, as a principle, with the same reference numerals, and the explanation thereof is omitted. The specific computational formulas and computational procedure disclosed hereinbelow need to be changed, as appropriate, according to the configuration of the device where the invention is to be used and various conditions, and the scope of the invention is not intended to be limited to the following description.

Figure 2:
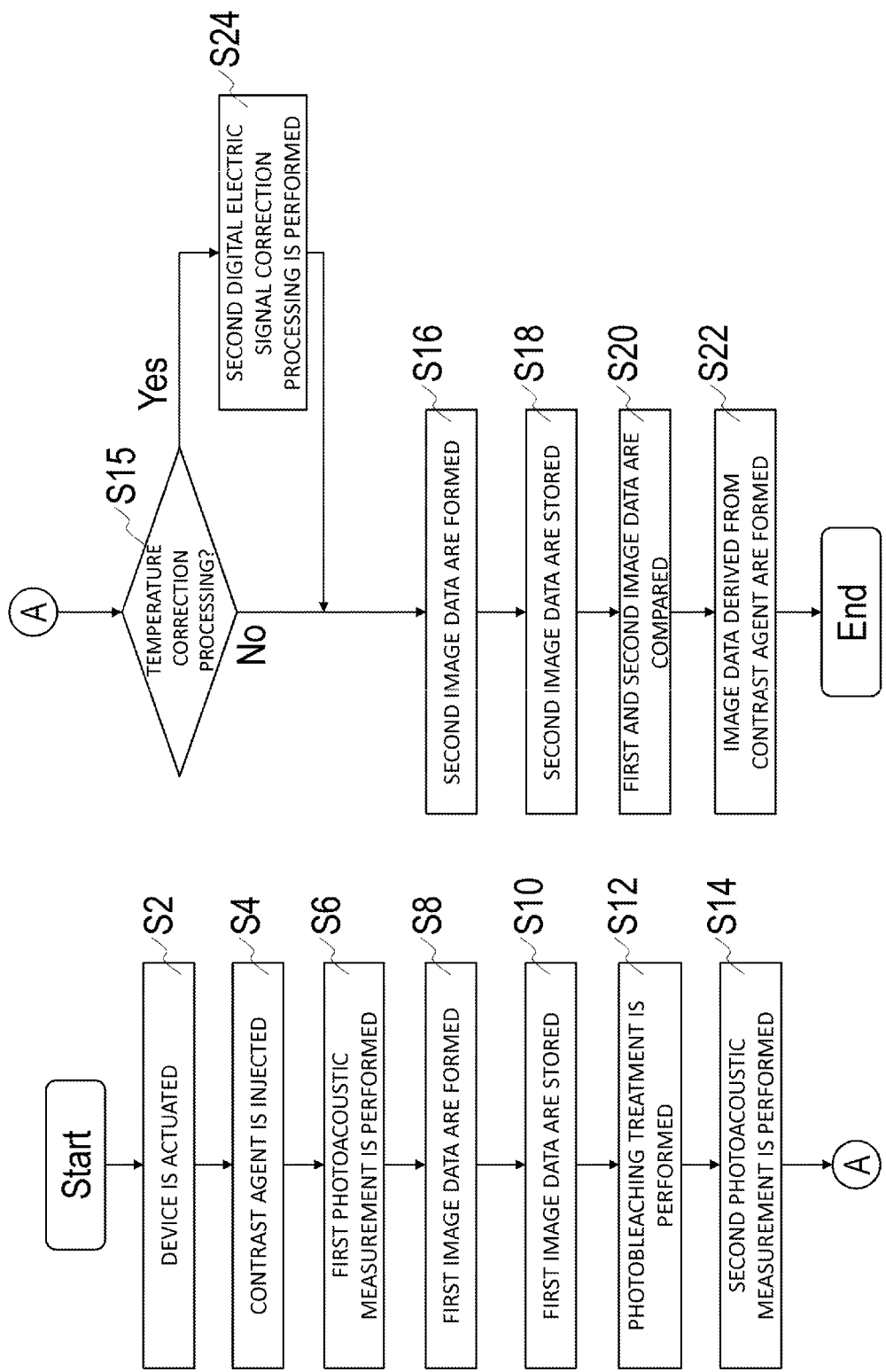
FIG. 2 is a flowchart illustrating the functions of a device 100 in Example 1 of the present invention.

The photoacoustic device in accordance with the present invention is inclusive of devices using a photoacoustic effect according to which an acoustic wave generated inside an object under irradiation with light (electromagnetic wave) such as near-IR radiation is received and information on the object is acquired as an image signal (also referred to as "image data"). A series of procedures of receiving the acoustic wave generated inside an object under irradiation with light (electromagnetic wave) such as near-IR radiation and acquiring information on the object as an image signal may be referred to as photoacoustic measurements or photoacoustic tomography (PAT) measurements. For convenience of explanation, a series of operations involving irradiating an object with light, receiving an acoustic wave on the basis of this irradiation, and acquiring a digital electric signal on the basis of the received wave, for example, as illustrated by FIG. 2, will be also referred to, as appropriate, as photoacoustic measurements.

The information on the object acquired in a device using the photoacoustic effect (photoacoustic device) represents the generation source distribution of acoustic waves induced by light irradiation. Alternatively, it represents the initial source pressure distribution within the object, or the light energy absorption density distribution or absorption coefficient distribution derived from the initial source pressure distribution, and the concentration distribution of substances constituting the tissue. The substance concentration distribution, as referred to herein, is for example, the oxygen saturation degree distribution, total hemoglobin concentration distribution, oxidized-reduced hemoglobin concentration distribution, and contrast agent concentration distribution.

Further, property information which is information on the object relating to a plurality of locations may be also acquired as a two-dimensional or three-dimensional property distribution. The property distribution can be acquired as an image signal indicating property information within the object.

The acoustic wave, as referred to in the present invention, is typically an ultrasonic wave and is inclusive of elastic waves which are called sound waves and ultrasonic waves. An acoustic wave generated by the photoacoustic effect is referred to as a photoacoustic wave of photo-ultrasonic wave. An acoustic detector (for example, a probe) receives an acoustic wave generated or reflected inside the object.

Example 1

FIG. 1 is a block diagram illustrating Example 1 of the photoacoustic device according to an embodiment of the present invention. A photoacoustic device 100 of Example 1 (referred to hereinbelow as "device 100") has a light source 2, a mirror 6, and an irradiation unit 8. The device 100 also has a probe (corresponds to a receiving unit) 22, a signal collection unit (corresponds to part of an acquisition unit) 24, a signal processing unit (corresponds to another part of the acquisition unit) 26, and a display unit 28. Three light absorbers defined hereinbelow are used in the explanation. Thus, the three light absorbers are defined in the following manner. Thus, defined are a contrast agent 14 which is an artificial light absorber, a non-artificial absorber 12 (referred to hereinbelow as "absorber 12") which is a light absorber other than the contrast agent 14, and a combined absorber 16 (referred to hereinbelow as "absorber 16") which is a light absorber in which the two aforementioned absorbers are combined.

<<Light Source 2>>

The light source 2 emits a light 4, which is a pulsed light, when an acoustic wave is generated from an object 20, and emits a light 30, which is a pulsed light different from the light 4, when the contrast agent 14 is bleached. However, such a configuration is not limiting, and the device 100 may be configured such that the light 4 is emitted by the light source 2 and the light 30 is emitted by another light source. Such a configuration is described hereinbelow. When the object 20 is a living body, the wavelength of the light 4 is a specific wavelength that can be absorbed by a light absorber, for example, blood which is the absorber 12 or the contrast agent 14 inside the living body. The temporal pulse width (pulse ON time and high-level time width) of the light 4 is preferably of the order of several nanoseconds to several hundred nanoseconds. The pulse interval (low-level time width) of the pulsed light of the light 4 is taken as an OFF time. The light source 2 is preferably configured of a laser (laser device). However, such a configuration is not limiting, and a light-emitting diode can be used instead of the laser. Various lasers, for example, a solid-state layer, gas laser, dye laser, or semiconductor laser, can be used as the light source 2.

The light source 2 may be constituted by a single light source or by a plurality of light sources. The advantage of constituting the light source 2 by a plurality of light sources is that the intensity of the light by which the object 20 is irradiated is increased. In this case, the light source 2 may be constituted by providing a plurality of light sources capable of generating the light of a substantially the same wavelength. The light source 2 may be configured to be capable of generating light while switching between a plurality of wavelengths. A plurality of light sources that differ in the generated wavelength may be also used. In this case, where the device 100 performs photoacoustic measurements for each wavelength with the light source 2, it is possible to acquire optical property value distributions that differ depending on the wavelength and also acquire an oxygen saturation degree on the basis of the optical property value distributions. When the light source 2 is configured to be capable of generating light while switching between a plurality of wavelengths, the light source may be configured of a laser using optical parametric oscillators (OPOs) or dyes capable of switching the generated wavelength.

The wavelength of the light 4 is preferably within a wavelength region from 600 nm to 1300 nm in which the light can be easily selectively absorbed by the contrast agent 14 and absorber 12 contained in the living body which is the object 20. Further, when the optical property value distribution of a living body tissue which is relatively close to the living body surface is to be determined, the wavelength of the light 4 is preferably within a wavelength region, for example, from 400 nm to 1600 nm, which is wider than the abovementioned wavelength region. From the standpoint of efficiently confining the absorption energy in the absorber 12 or contrast agent 14, it is preferred that the temporal pulse width of the light 4 satisfy a heat-stress confinement condition. The temporal pulse width of the light 4 is, for example, about 1 nanosecond to 200 nanoseconds. When the absorber 12, contrast agent 14, or absorber 16 absorb light energy, the temperature thereof rises and it generates an acoustic wave due to volume expansion caused by the rise in temperature thereof.

The wavelength of the light 30 is such that the light can be absorbed by the contrast agent 14. Such a wavelength is preferably within about 50 nm from the maximum absorption wavelength of the contrast agent 14, more preferably within about 20 nm from the maximum absorption wavelength of the contrast agent 14. The pulse interval of the light 30 is preferably shorter than the triplet excited state relaxation time of the contrast agent 14. For example, in the case of ICG, it is preferred that the pulse interval (low-level time of the light 30) of the light 30 be 0.7 milliseconds or less. When the pulse interval of the light 30 is constant, it is preferred that the pulse width τ of the light 30 and the pulse frequency f of the light 30 satisfy the following mathematical formula (II).

$$(1-\tau \cdot f)/f < 7 \times 10^{-4} \quad \text{(II)}$$

The light source 2 may be configured to be capable of generating continuous light. In such a case, the contrast agent 14 may be photobleached more efficiently. The continuous light may be, for example, light that is outputted stationary with a constant intensity, rather than in the form of pulses. In most of organic dyes, the absorption of light of sufficient intensity from the outside causes the energy transition from a ground state S0 to an excited state S1. The contrast agent 14 of the present example is constituted by such an organic dye. When the energy transition proceeds from the excited state S1 to the ground state S0 in such an organic dye, part of the absorbed light energy is released as fluorescence and part as thermal-oscillation energy. Meanwhile, the internal relaxation (also referred to as intersystem crossing) in such an organic dye causes energy transition from the state S1 to the so-called triplet excited state T1. The main cause of photobleaching is the decomposition of the organic dye caused by interaction with oxygen in the surroundings in the state T1. Further, the energy transition from the state S1 to the state S0 proceeds in several nanoseconds, whereas the energy transition from the state T1 to the state S0 proceeds after comparatively stable retention time of several microseconds.

The energy transition from the state S0 to the state S1 or state T1 in the contrast agent 14 proceeds at the following speed. Thus, this speed is greater than that of the energy transition from the state T1 of the contrast agent 14 to the state S0 induced by the irradiation of the contrast agent 14 with continuous light or light 30 with the pulse width τ and pulse frequency f fulfilling the condition represented by mathematical formula (II). Therefore, the amount of the contrast agent 14 in the state T1 increases and the efficiency of photobleaching reaction rises. This result is clearly demonstrated by the below-described examples. The photobleaching of the contrast agent 14 in the state T1 is advanced by the interaction with oxygen in the surrounding environment. Therefore, in a region with a low oxygen concentration (for example, a region where a tumor such as cancer is present is generally in a low-oxygen state), the triplet excited state relaxation time is longer than that in the region with a high oxygen concentration. Furthermore, in a high-viscosity region (for example, in blood or intercellular substances, a region higher in viscosity than water), the diffusion rate of oxygen decreases, and therefore the triplet excited state relaxation time becomes longer than that in a low-viscosity region. The light quantity of the light 30 is preferably as large as possible while being equal to or less than the maximum permissible exposure (can be abbreviated hereinbelow as MPE). The photobleaching of the contrast agent 14 can thus be efficiently advanced.

The device 100 can be used for therapy of a human or an animal which is the object 20. As will be mentioned hereinbelow, the device 100 may be configured to have a light source to be used for photoacoustic measurements and a light source generating a laser beam for photobleaching a contrast agent. The device 100 can thus be configured to perform photodynamic therapy. Alternatively, the device 100 can be configured also to perform therapy using light (photothermal therapy). The therapeutic effect of the photodynamic therapy is known to be mainly caused by reactive oxygen species generated on the basis of oxygen in a singlet excited state (also referred to as singlet oxygen). The singlet oxygen is generated by the interaction between an organic dye, which has assumed a first excited triplet state (T1) due to absorption of a specific light, with oxygen in the vicinity thereof. In the process of inducing the photobleaching of the contrast agent 14 in the device 100, the contrast agent 14 assumes the first excited triplet state (T1) and generates the singlet oxygen, and the reactive oxygen species are then created by the generated singlet oxygen. As a result, the therapeutic effect of photodynamic therapy can be expected. The device 100 also demonstrates the effect of raising the temperature of the object (light irradiation segment) and the contrast agent 14 due to irradiation with the laser beam. Therefore, the therapeutic effect of photothermal therapy can be also expected.

<<Optical System 36>>

The optical system 36 is constituted by a mirror 6 and an irradiation unit 8. The mirror 6 guides the lights 4 and 30 emitted by the light source 2 to the irradiation unit 8. The irradiation unit 8 is constituted by optical components such as lenses, processes the guided lights 4 and 30 to obtain a light 10 with the desired light distribution shape, and irradiates the object 20 with the produced light. Such a configuration is, however, not limiting, and the optical system 36 may be also constituted by an optical waveguide such as an optical fiber through which the lights 4 and 30 emitted from the light source 2 are caused to propagate and guided from the light source 2 to the irradiation unit 8. Thus, the optical system 36 may be constituted, for example, by a mirror reflecting the lights 4 and 30, a lens that focuses or expands the lights 4 and 30 to change the shape thereof, and a diffusion plate that diffuses the light. Such a configuration is, however, not limiting, and any optical components can be used that are capable of shaping, as desired, the lights 4 and 30 emitted from the light source 2, so as to enable the irradiation of the object 20. From the standpoint of safety for the living body and enlargement of the diagnosis area, it is preferred that the lights 4 and 30 be expanded to a certain area by focusing with a lens.

<<Object 20>>

Although the object 20 does not constitute the device 100, it is described herein for the convenience of explanation. The object 20 is a living body, for example, a target segment for diagnosis of a living body, for example, a breast, a finger, or a limb of a human body or an animal. The device 100 may be used for diagnosis or process observations in chemical treatment of malignant tumors and vascular diseases of humans and animals.

<<Absorbers 12, 14, and 16>>

The absorber 12 is a living-body-derived non-artificial absorber and can be, for example, oxidized hemoglobin and reduced hemoglobin, or blood vessels including large amounts thereof, which are inherently present inside the object 20. The contrast agent 14 is an artificial light absorber administered from the outside of the object 20. A variety of artificial light absorbers which have properties of contrast agents may be used instead of the contrast agent 14. The contrast agent 14 is capable of being photobleached by the absorbed light 30. The contrast agent 14 is, for example, an organic dye and is preferably capable of absorbing light in a near-IR wavelength region which demonstrates a comparatively high transmissivity with respect to a human body. The near-IR wavelength region is a wavelength region from 600 nm to 1300 nm. Suitable examples of the contrast agent 14 include azine dyes, acridine dyes, triphenylmethane dyes, xanthene dyes, porphyrin dyes, cyanine dyes, and phthalocyanine dyes. Alternatively, styryl dyes, pyrylium dyes, azo dyes, quinone dyes, tetracycline dyes, flavone dyes, polyene dyes, BODIPY® dyes, and indiboid dyes may be used. The contrast agent 14 may be also indocyanine green (ICG) and Alexa Fluor® dyes such as Alexa Fluor® 750 (manufactured by Life Technologies Japan, Ltd.). Other examples include Cy® dyes (manufactured by GE Healthcare Inc.) and IR-783, IR-806, and IR-820 (manufactured by Sigma Aldrich Japan LLC). IRDye 800CW® and IRDye 800RS® (manufactured by LI-COR Inc.) and ADS780WS may be also used. Other examples include ADS795WS, ADS830WS, ADS832WS (manufactured by American Dye Source, Inc.), DyLight® dyes (manufactured by Thermo Fisher Scientific Inc.). Hilyte Fluor® dyes (manufactured by AnaSpec, Inc.) and DY® dyes (manufactured by Dyomics Co.) may be also used. For convenience of explanation, the absorber 16 is defined as a combination of the absorber 12 and the absorber 14, but actually present are the absorbers 12 and 14.

The molar extinction coefficient at the absorption maximum wavelength of the cyanine dye in the present embodiment is preferably $10^6$ $M^{-1}$ $cm^{-1}$ or more. The following general formulas (1) to (4) represent structural examples of cyanine dyes in the present embodiment.

[Chem. 1]

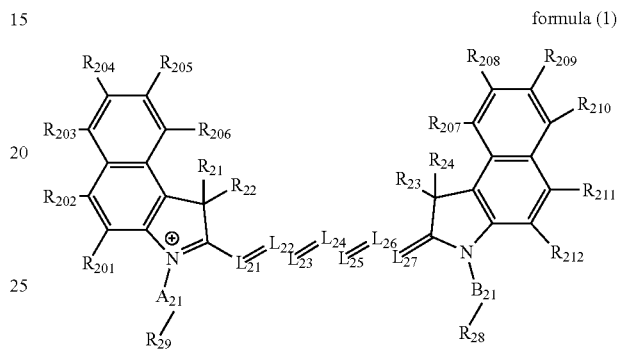

formula (1)

In formula (1), $R_{201}$ to $R_{212}$ are each independently a hydrogen atom, a halogen atom, $SO_3T_{201}$, $PO_3T_{201}$, a benzene ring, a thiophene ring, a pyridine ring or a linear or branched alkyl group with a carbon number of 1 to 18. Here, $T_{201}$ represents any one of a hydrogen atom, a sodium atom, and a potassium atom. In formula (1), $R_{21}$ to $R_{24}$ are each independently a hydrogen atom or a linear or branched alkyl group with a carbon number of 1 to 18. In formula (1), $A_{21}$ and $B_{21}$ are each independently a linear or branched alkylene group with a carbon number of 1 to 18. In formula (1), $L_{21}$ to $L_{27}$ are each independently CH or $CR_{25}$. The $R_{25}$ represents a linear or branched alkyl group with a carbon number of 1 to 18, a halogen atom, a benzene ring, a pyridine ring, a benzyl group, $ST_{202}$, or a linear or branched alkylene group with a carbon number of 1 to 18. The $T_{202}$ represents a linear or branched alkyl group with a carbon number of 1 to 18, a benzene ring, or a linear or branched alkylene group with a carbon number of 1 to 18. In formula (1), $L_{21}$ to $L_{27}$ may form a 4-membered to 6-membered ring.

In formula (1), $R_{28}$ represents any one of —H, —OCH$_3$, —NH$_2$, —OH, —CO$_2$T$_{28}$, —S(=O)$_2$OT$_{28}$, —P(=O)(OT$_{28}$)$_2$, —CONH—CH(CO$_2$T$_{28}$)-CH$_2$(C=O)OT$_{28}$, —CONH—CH(CO$_2$T$_{28}$)-CH$_2$CH$_2$ (C=O)OT$_{28}$, and —OP(=O)(OT$_{28}$)$_2$. The T$_{28}$ represents any one of a hydrogen atom, a sodium atom, and a potassium atom. In formula (1), $R_{29}$ is any one of —H, —OCH$_3$, —NH$_2$, —OH, —CO$_2$T$_{29}$, —S(=O)$_2$OT$_{29}$, —P(=O)(OT$_{29}$)$_2$, —CONH—CH(CO$_2$T$_{29}$)-CH$_2$ (C=O)OT$_{29}$, —CONH—CH(CO$_2$T$_{29}$)-CH$_2$CH$_2$ (C=O)OT$_{29}$, and —OP(=O)(OT$_{29}$)$_2$. The T$_{29}$ represents any one of a hydrogen atom, a sodium atom, and a potassium atom.

[Chem. 2]

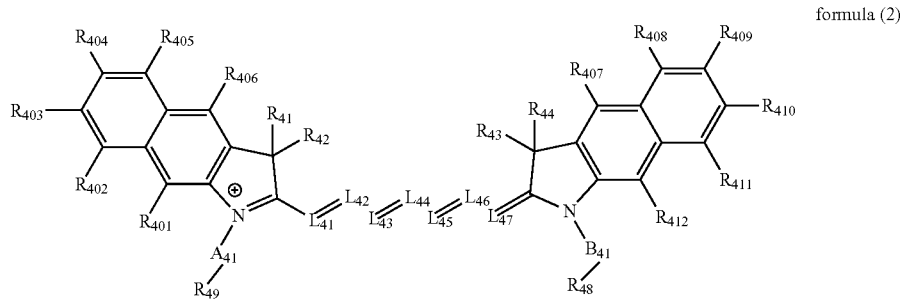

formula (2)

In formula (2), $R_{401}$ to $R_{412}$ are each independently a hydrogen atom, a halogen atom, $SO_3T_{401}$, $PO_3T_{401}$, a benzene ring, a thiophene ring, a pyridine ring, or a linear or branched alkyl group with a carbon number of 1 to 18. The $T_{401}$ represents any one of a hydrogen atom, a sodium atom, and a potassium atom. In formula (2), $R_{41}$ to $R_{44}$ are each independently a hydrogen atom or a linear or branched alkyl group with a carbon number of 1 to 18. In formula (2), $A_{41}$ and $B_{41}$ are each independently a linear or branched alkylene group with a carbon number of 1 to 18. In formula (2), $L_{41}$ to $L_{47}$ are each independently CH or $CR_{45}$. The $R_{45}$ represents a linear or branched alkyl group with a carbon number of 1 to 18, a halogen atom, a benzene ring, a pyridine ring, a benzyl group, $ST_{402}$, or a linear or branched alkylene group with a carbon number of 1 to 18. The $T_{402}$ represents a linear or branched alkyl group with a carbon number of 1 to 18, a benzene ring, or a linear or branched alkylene group with a carbon number of 1 to 18. In formula (2), $L_{41}$ to $L_{47}$ may form a 4-membered to 6-membered ring. In formula (2), $R_{48}$ is any one of —H, —OCH$_3$, —NH$_2$, —OH— CO$_2$T$_{48}$, —S(=O)$_2$OT$_{48}$, —P(=O)(OT$_{48}$)$_2$, —CONH— CH(CO$_2$T$_{48}$)-CH$_2$ (C=O)OT$_{48}$, —CONH—CH(CO$_2$T$_{48}$)- CH$_2$CH$_2$ (C=O)OT$_{48}$, and —OP(=O)(OT$_{48}$)$_2$. The T$_{48}$ represents any one of a hydrogen atom, a sodium atom, and a potassium atom. In formula (2), $R_{49}$ is any one of —H, —OCH$_3$, —NH$_2$, —OH, —CO$_2$T$_{49}$, —S(=O)$_2$OT$_{49}$, —P(=O)(OT$_{49}$)$_2$, —CONH—CH(CO$_2$T$_{49}$)-CH$_2$ (C=O) OT$_{49}$, —CONH—CH(CO$_2$T$_{49}$)-CH$_2$CH$_2$(C=O)OT$_{49}$, and —OP(=O)(OT$_{49}$)$_2$. The T$_{49}$ represents any one of a hydrogen atom, a sodium atom, and a potassium atom.

In formula (3), $R_{601}$ to $R_{612}$ are each independently a hydrogen atom, a halogen atom, $SO_3T_{601}$, $PO_3T_{601}$, a benzene ring, a thiophene ring, a pyridine ring, or a linear or branched alkyl group with a carbon number of 1 to 18. The $T_{601}$ represents any one of a hydrogen atom, a sodium atom, and a potassium atom. In formula (3), $R_{61}$ to $R_{64}$ are each independently a hydrogen atom or a linear or branched alkyl group with a carbon number of 1 to 18. In formula (3), $A_{61}$ and $B_{61}$ are each independently a linear or branched alkylene group with a carbon number of 1 to 18. In formula (3), $L_{61}$ to $L_{67}$ are each independently CH or $CR_{65}$. The $R_{65}$ represents a linear or branched alkyl group with a carbon number of 1 to 18, a halogen atom, a benzene ring, a pyridine ring, a benzyl group, $ST_{602}$, or a linear or branched alkylene group with a carbon number of 1 to 18. The $T_{602}$ represents a linear or branched alkyl group with a carbon number of 1 to 18, a benzene ring or a linear or branched alkylene group with a carbon number of 1 to 18. In formula (3), $L_{61}$ to $L_{67}$ may form a 4-membered to 6-membered ring. In formula (3), $R_{68}$ is any one of —H, —OCH$_3$, —NH$_2$, —OH, —CO$_2$T$_{68}$, —S(=O)$_2$OT$_{68}$, —P(=O)(OT$_{68}$)$_2$, —CONH— CH(CO$_2$T$_{68}$)-CH$_2$ (C=O)OT$_{68}$, —CONH—CH(CO$_2$T$_{68}$)- CH$_2$CH$_2$ (C=O)OT$_{68}$, and —OP(=O)(OT$_{68}$)$_2$. The T$_{68}$ represents any one of a hydrogen atom, a sodium atom, and a potassium atom. In formula (3), $R_{69}$ is any one of —H, —OCH$_3$, —NH$_2$, —OH, —CO$_2$T$_{69}$, —S(=O)$_2$OT$_{69}$, —P(=O)(OT$_{69}$)$_2$, —CONH—CH(CO$_2$T$_{69}$)-CH$_2$ (C=O) OT$_{69}$, —CONH—CH(CO$_2$T$_{69}$)-CH$_2$CH$_2$(C=O)OT$_{69}$, and —OP(=O)(OT$_{69}$)$_2$. The T$_{69}$ represents any one of a hydrogen atom, a sodium atom, and a potassium atom

[Chem. 3]

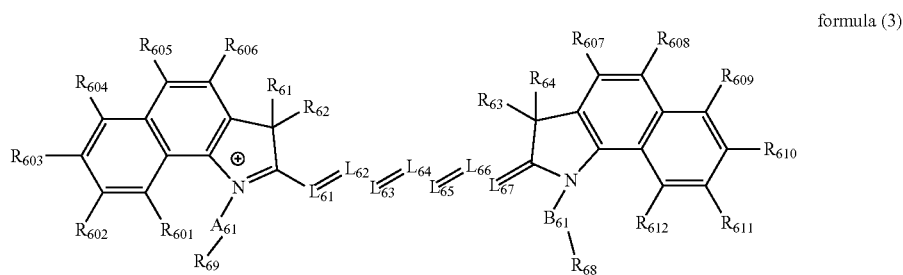

formula (3)

[Chem. 4]

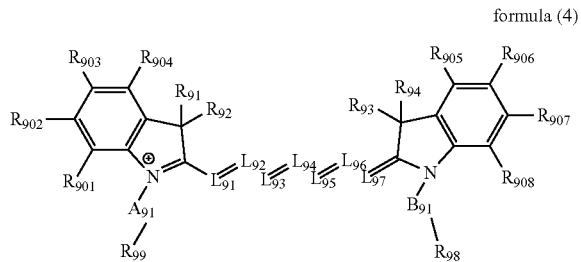

formula (4)

In formula (4), $R_{901}$ to $R_{908}$ are each independently a hydrogen atom, a halogen atom, $SO_3T_{901}$, $PO_3T_{901}$, a benzene ring, a thiophene ring, a pyridine ring, or a linear or branched alkyl group with a carbon number of 1 to 18. The $T_{901}$ represents any one of a hydrogen atom, a sodium atom, and a potassium atom. In formula (4), $R_{91}$ to $R_{94}$ are each independently a hydrogen atom or a linear or branched alkyl group with a carbon number of 1 to 18. In formula (4), $A_K$ and $B_{91}$ are each independently a linear or branched alkylene group with a carbon number of 1 to 18. In formula (4), $L_{91}$ to $L_{97}$ are each independently CH or $CR_{95}$. The $R_{95}$ is any one of a linear or branched alkyl group with a carbon number of 1 to 18, a halogen atom, a benzene ring, a pyridine ring, a benzyl group, $ST_{902}$, or a linear or branched alkylene group with a carbon number of 1 to 18. The $T_{902}$ represents a linear or branched alkyl group with a carbon number of 1 to 18, a benzene ring, or a linear or branched alkylene group with a carbon number of 1 to 18. In formula (4), $L_{91}$ to $L_{97}$ may form a 4-membered to 6-membered ring. In formula (4), $R_{98}$ is any one of —H, —OCH$_3$, —NH$_2$, —OH—CO$_2$T$_{98}$, —S(=O)$_2$OT$_{98}$, —P(=O)(OT$_{98}$)$_2$, —CONH—CH(CO$_2$T$_{98}$)-CH$_2$ (C=O)OT$_{98}$, —CONH—CH(CO$_2$T$_{98}$)-CH$_2$CH$_2$ (C=O)OT$_{98}$, and —Op (=O)(OT$_{98}$)$_2$. The $T_{98}$ represents any one of a hydrogen atom, a sodium atom, and a potassium atom. In formula (4), $R_{99}$ is any one of —H, —OCH$_3$, —NH$_2$, —OH, —CO$_2$T$_{99}$, —S(=O)$_2$OT$_{99}$, —P(=O)(OT$_{99}$)$_2$, —CONH—CH (CO$_2$T$_{99}$)-CH$_2$ (C=O)OT$_{99}$, —CONH—CH(CO$_2$T$_{99}$)-CH$_2$CH$_2$(C=O)OT$_{99}$, and —OP(=O)(OT$_{99}$)$_2$. The $T_{99}$ represents any one of a hydrogen atom, a sodium atom, and a potassium atom.

Embodiments of cyanine dyes in the present embodiment include indocyanine green, SF-64 having a benzotricarbocyanine structure represented by chemical formula 1, and compounds represented by chemical formulas (i) to (v).

[Chem. 5]

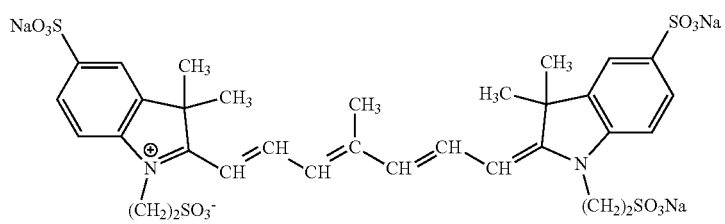

chemical formula (i)

[Chem. 6]

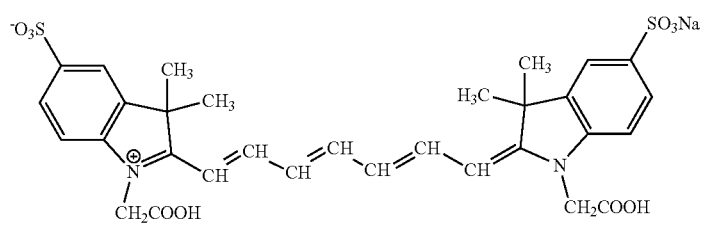

chemical formula (ii)

[Chem. 7]

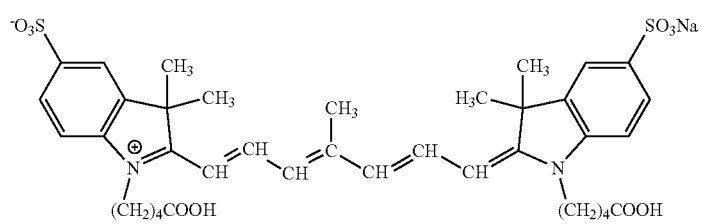

chemical formula (iii)

-continued

[Chem. 8]

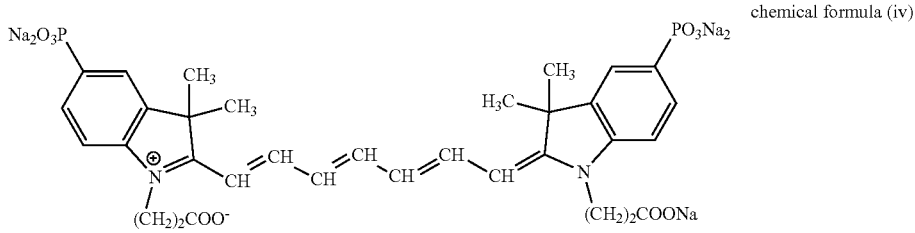

chemical formula (iv)

[Chem. 9]

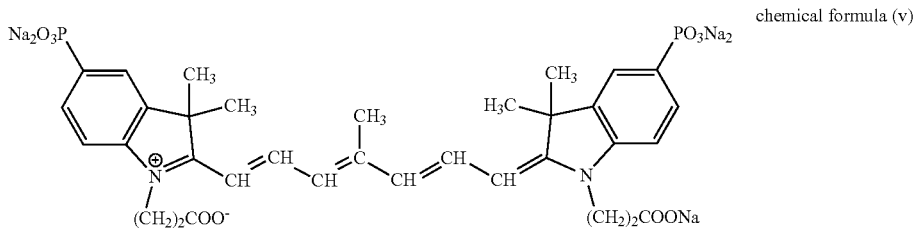

chemical formula (v)

In the cyanine dye, the aromatic ring may be substituted with a sulfonic acid group, a carboxyl group, or a phosphoric acid group. A sulfonic acid group, a carboxyl group, and a phosphoric acid group may be also introduced in a portion other than the aromatic ring.

The contrast agent 14 may be administered to the object 20 by a health care worker. Alternatively, the device 100 may be equipped with an injection unit such that has a well-known injection system or injector for automatically injecting the contrast agent 14.

<<Probe 22>>

The probe 22 is an acoustic wave detector that detects an acoustic wave generated in the surface portion of the object 20 and inside thereof when the surface of the object 20 is irradiated with the light 4. The probe 22 receives the acoustic wave with a conversion element of the probe, converts the received acoustic wave into an analog electric signal, and transmits the analog electric signal to a signal collection unit 24. A variety of conversion elements capable of detecting the acoustic wave can be used, examples thereof including a piezoelectric element (piezoelement) which uses a piezoelectric effect, an element using light resonance, and an element using changes in capacitance. The probe 22 is preferably configured by a plurality of conversion elements arranged one- or two-dimensionally. As a result of configuring the probe 22 of a multidimensional element array constituted by such a plurality of conversion element, it is possible to detect the acoustic wave at a plurality of locations at the same time, shorten the detection time, and reduce the adverse effect produced by vibrations of the object 20 on the reconstructed image signal.

It is preferred that the probe 22 be capable of detecting the acoustic wave, which propagates from the object 20, from all direction. In such a case, the amount of data sufficient for image reconstruction can be uniformly ensured from the entire object 20. For this purpose, the probe 22 is configured to be movable to positions for acquiring the acoustic wave along the rear surface of the object 20 with a drive device such as a stepping motor or a motor capable of moving the probe continuously. Such a configuration is, however, not limiting, and the drive device may be configured to be capable of moving the probe 22 to any position. Further, the probe 22 may be configured to have the below-described substantially spherical crown shape.

The probe 22 may have a multi-probe configuration in which 128 conversion elements are provided and those conversion elements are arranged two-dimensionally. Where such a multi-probe receives acoustic waves while moving around the object 20, it is possible to receive acoustic waves sufficient for obtaining information relating to the spatial arrangement of sound sources inside the object 20. When the probe 22 is such a multi-probe, for example, the acoustic wave is received at each acoustic wave reception position where 120 probes 22 need to be positioned around the object 20. In such a case, the probe 22 is substantially identical to a probe in which the acoustic waves from the object 20 are converted into analog electric signals by a total of 15,360 conversion elements. Such a configuration is, however, not limiting, and the drive device may move the object 20 relative to the probe 22. Alternatively, the drive device may move the object 20 and the probe 22 relative to each other to obtain the positional relationship of the probe 22 and the object 20 such that the acoustic wave can be advantageously acquired. In this case, the probe 22 may receive the acoustic wave in such a positional relationship.

<<Signal Collection Unit 24>>

The signal collection unit 24 is constituted by an analog/digital converter (referred to hereinbelow as "ADC") and an amplifier. The ADC inputs the analog electric signal transmitted from the probe 22, converts this analog electric signal into a digital electric signal, and transmits the digital electric signal to the amplifier. The amplifier amplifies, with a predetermined gain, the digital electric signal transmitted from the ADC, and transmits the amplified digital signal to the signal processing unit 26. Such a configuration is, however, not limiting, and the signal collection unit 24 may be configured of a field programmable gate array (FPGA) chip. When a plurality of analog electric signals is transmitted from the probe 22, it is preferred that the signal collection unit 24 be capable of parallel processing of those analog electric signals at the same time. In such a case, the signal processing time can be shortened and the time required to form the image signal can be also shortened.

<<Signal Processing Unit 26>>

The signal processing unit 26 has a storage unit for successively storing digital electric signals transmitted form the signal collection unit 24, and a reconstruction unit that generates an image signal by reading the digital electric signals which have been stored and performing image reconstruction processing with respect to the digital electric signals which have been read. The signal processing unit 26 may further have a temperature correction unit. The temperature correction unit measures the increase in temperature of the object 20, which is caused by the irradiation of the object 20 with the light 30, from the irradiation energy amount of the light 30 when the contrast agent 14 located inside the object 20 is photobleached. On the basis of the measured value, the temperature correction unit corrects the digital electric signal, image signal, or brightness value, contrast, or intensity which are image feature amounts of the displayed image which is to be displayed by the display unit 28. The image processing unit 26 also has a computational unit that performs differential computations.

The differential computations are performed by the computational unit between the image signal based on the first photoacoustic measurement and the image signal based on the second photoacoustic measurement performed after photobleaching with the light 30. Those image signals are formed by two- or three-dimensionally specifying the pixel values of an image feature amount. The image feature amount may be a brightness value or a contrast value. The differential computations find the difference between the brightness value at a certain coordinate of an image signal based on the first photoacoustic measurements, which is one image signal, and the brightness value at the coordinate of an image signal based on the second photoacoustic measurements, which is the other image signal, this coordinate being the same coordinate as that of the one image signal. The differential computations acquire a difference value on the basis of the subtraction result. In the differential computations, the processing of obtaining the difference is then performed for all of the coordinates. However, such a procedure is not limiting, and the differential computations may be performed in the following manner. Thus, a difference is determined between a digital electric signal stored in a memory at a former stage before the one image signal is formed and a digital electric signal (signal serving as a basis of the image signal) which has been stored in the memory before the other image signal has been formed. Further, a signal component originating from the contrast agent 14 in the digital electric signal acquired during the first photoacoustic measurement corresponds to the amount of reduction in the digital electric signal between the first photoacoustic measurement and second photoacoustic measurement. Therefore, the signal component originating from the contrast agent 14 may be acquired, for example, by acquiring a portion of the amount of reduction which is equal to or higher than a predetermined value. This predetermined value may be set, as appropriate, at random by the user.

Further, the device 100 may repeat n times (n is a natural number) a series of procedures involving the photobleaching treatment of the contrast agent 14 by irradiation with the light 30 after the first photoacoustic measurement, then the second photoacoustic measurement, and then the differential computations. This is because by calculating the change amount between the differential computation results on the basis of n differential computation results, the computational unit can acquire, with higher accuracy, the digital electric signals derived substantially only from the contrast agent 14. Further, when image signals are formed by image reconstruction of the digital electric signals derived from the contrast agent 14 and based on the differential computation results, the differential computation results may be acquired on the basis of image similarity.

<<Display Unit 28>>

The display unit 28 inputs the image signals transmitted from the signal processing unit 26 and forms a visually recognizable displayed image on the basis of the image signals. The display unit 28 is, for example, a liquid crystal display, a plasma display, a LED display, or an organic EL display. However, this list is not limiting, and the display unit 28 may be provided separately from the device 100.

<Temperature Correction>

In the device 100, the object 20 is irradiated with the light 30 between the first photoacoustic measurement and second photoacoustic measurement to photobleach the contrast agent 14 inside the object 20. In this case, the temperature of the object 20 itself is raised by the irradiation with the light 30. This increase in temperature results at least in the increase in speed c of sound and volume expansion coefficient $\beta$ of the object 20. In this case, the Gruneisen parameter $\Gamma$ increases due to the increase in the speed c of sound and volume expansion coefficient $\beta$.

For this reason, the device 100 may have a temperature correction unit that corrects the digital electric signal acquired during the second photoacoustic measurement on the basis of the increase in temperature of the object 20 and may form the image signal on the basis of the corrected digital electric signal. Alternatively, the temperature correction unit may be configured to correct the image signal formed from the digital electric signal acquired during the second photoacoustic measurement, the correction being performed on the basis of the increase in temperature of the object 20. As a result, the deviation from the desired value among the digital electric signal obtained by the second photoacoustic measurement caused by the increase in temperature, this deviation being caused by the increase in temperature, can be corrected on the basis of changes in the speed c of sound, volume thermal expansion coefficient $\beta$, and the Gruneisen parameter $\Gamma$ caused by the increase in temperature. This deviation increases with the rise amount in the increase in temperature. The desired value may be a digital electric signal that would be obtained by photoacoustic measurement when there is no increase in temperature, the photoacoustic measurement being the second photoacoustic measurement.

The temperature correction unit measures the increase in temperature of the object 20 by the following method. This measurement method performed by the temperature correction unit may be invasive and non-invasive. With the invasive measurement method, for example, a temperature-measuring terminal such as a thermocouple of thermistor is inserted into the object 20. With the non-invasive measurement method, the measurements are performed, for example, by using MRI, microwave CT, or radiometry. In the method for measuring the increase in temperature of the present embodiment, the energy absorbed by the object 20 and the energy lost from the absorbed fraction are estimated from the energy of the light 30 to measure the increase in temperature of the object 20. More specifically, with this measurement method, the increase in temperature is determined by solving a differential equation relating to energy conservation. The increase in temperature of the object 20 under irradiation with the light 30 is represented by the following Math. Equation III including the density $\rho$ and heat capacity $C_p$ of the object 20 and the energy $E_a'$ absorbed by the object 20.

$$\Delta T = E_a'/(\rho C_p) \tag{III}$$

The energy $E_a'$ absorbed by the object 20 is represented by the following Math. Equation IV including the absorption coefficient μa of the light absorber and the light quantity Φ at the position of the light absorber.

$$E_a' = \mu a \cdot \Phi \qquad (IV)$$

The energy of the light 30 by which the object 20 is irradiated from the outside decreases exponentially inside the object 20. Meanwhile, the loss of energy of the light 30 by which the object 20 is irradiated from the outside is generated on the basis of heat transport (for example, heat transport between the surface of the object 20 and the outside) and thermal conduction (inside the object 20) which are caused by the difference in temperature between the segment where the temperature of the object 20 rises and the surroundings thereof. The increase in temperature is measured by estimating the increase in temperature of the object 20 from the energy of radiated light 30 by solving a set of such differential equations.

FIG. 2 is a flowchart illustrating functions of the device 100 in Example 1 of the present invention. The flow starts from holding the object 20 with the device 100. In this case, when the device 100 is configured to include two plates, the object 20 may be held between the two plates, and when the probe 22 is configured in the below-described substantially spherical crown shape, the object 20 may be held by inserting into a cup.

In step S2, electric power is supplied to the device 100 in a state in which the object 20 is held by the device 100, and the process advances to step S4. Such a flow is, however, not limiting, and the object 20 may be held, according to the functions of the device 100, after the power has been supplied to the device 100. This is because where the object 20 is a living human being, a load applied thereto can be reduced by automatically adjusting the hardness of the object 20 or the holding position with the device 100. In step S4, the contrast agent 14 is injected in the object 20 with the contrast agent injection unit provided to the device 100, and the process advances to step S6. However, the present invention is not limited to this, and the injection of the contrast agent 14 may be performed by a human.

In step S6, the object 20 including the contrast agent 14 is irradiated by the irradiation unit 8 with the light 10. The radiated light 10 is spread evenly across substantially the entire area of the surface of the object 20. This is done so to ensure efficient absorption of the light 10 by the absorbers 12, 14 inside the object 20. The probe 22 is then moved by the drive device along the rear surface of the object 20. While the probe is thus moved, the acoustic waves generated from the absorbers 12, 14 inside the object 20 under the irradiation with the light 10 are sequentially received by the conversion elements and converted into analog electric signals. The analog electric signals are sequentially transmitted to the signal collection unit 24. In this case, the drive device may move the probe 22 continuously or in a stepwise manner. When the probe 22 is moved in a stepwise manner, the light 10 may be radiated for each step of this stepwise movement, and the acoustic wave may be received in each radiation cycle. Such a procedure is, however, not limiting, and the light may be radiated while the irradiation unit 8 is moved along the surface of the object 20 synchronously with the probe 22. In such a case, the object 20 can be irradiated with the light 10 more uniformly over the entire area. Further, when the probe 22 is configured in a substantially spherical crown shape, the acoustic waves may be received by the probe 22 while the probe 22 is moved spirally. The analog electric signal transmitted in the above-described manner is converted into a digital electric signal by analog-digital conversion in the signal collection unit 24, and the converted signal is transmitted to the signal processing unit 26. The transmitted digital electric signals are sequentially stored in the memory inside the signal processing unit 26, and the process advances to step S8.

In step S8, an image signal is formed by performing the image reconstruction processing with respect to the digital electric signals stored in the memory, and the process then advances to step S12. This formation is performed herein by the universal back projection method, but various image reconstruction methods can be used. In step S12, the object 20 is irradiated for an arbitrary time with the laser beam 30 at or below the maximum permissible exposure. Under such irradiation, the contrast agent 14 present inside the object 20 is photobleached. In this case, the photobleaching results from the breakage of some of the bonds of the contrast agent 14 by the light 10. The process then advances to step S14. As a result of such processing, the generation of acoustic waves derived from the contrast agent 14 is reduced in the second photoacoustic measurement of the later stage.

In step S14, after the entire contrast agent 14 or the major part thereof in the object 20 has been photobleached, the second photoacoustic measurement similar to that of step S10 is performed, and the process advances to step S15. In this case, in the digital electric signal obtained by the photoacoustic measurement, the signal component derived from the contrast agent 14 is less than that in the digital electric signal of the first photoacoustic measurement, or is not present at all. In step S15, it is determined whether or not to correct the effect of the increase in temperature of the object 20 on the obtained digital electric signal. In this case, the temperature correction may be set by the user to be performed in advance. Alternatively, the device 100 may be equipped with a temperature measurement device capable of measuring the temperature invasively or non-invasively and it may be determined that the temperature correction processing is to be performed when the temperature of the object 20 is determined by the temperature measurement device to be equal to or higher than a predetermined temperature. Where it is determined in step S15 that the temperature correction is not to be performed, the process advances to step S16, and where it is determined that the temperature correction is to be performed, the process advances to step S24. In step S16, the image signal is formed by the same processing as that of step S8 from the digital electric signal which has not been subjected to the temperature correction, and the process advances to step S18. In step S18, the image signal is stored in the memory inside the signal processing unit 26 in the same manner as in step S10, and the process advances to step S20.

In step S24, the digital electric signal which is based on the second photoacoustic measurement and has been stored in the memory is read therefrom, and the digital electric signal which has been read is subjected to correction processing in the direction of reducing the effect of the increase in temperature. In the correction processing, the speed c of sound, volume expansion coefficient β, and Gruneisen parameter Γ of the object 20 at the time the temperature of the object 20 has dropped correspondingly to the increase in temperature (that is, the object 20 in the case in which the temperature is assumed not to rise) are calculated. Further, in the correction processing, the calculation results are divided by the respective values of the speed c of sound, volume expansion coefficient β, and Gruneisen parameter Γ of the object 20 which has increased in temperature. In the correction processing, the results obtained by the division are each further multiplied by the digital electric signal of the second photoacoustic measurement which has been read. As a result, the correction is performed in the direction of reducing the effect produced by the increase in the speed c of sound, volume expansion coefficient β, and Gruneisen parameter Γ demonstrated in response to the increase in temperature. Thus, the correction is performed such that the speed c of sound, volume expansion coefficient β, and Gruneisen parameter Γ obtained when the temperature has increased approach those obtained when the temperature of the object 20 has not increased. The digital electric signals formed by such multiplication are stored anew as corrected digital electric signals in the memory, and the process advances to step S16. In step S16, after this temperature correction processing, an image signal is formed by performing the image reconstruction processing same as described hereinbelow with respect to the corrected digital electric signal, and the process advances to step S18. In step S18, the image signal is stored in the memory in the signal processing unit 26, and the process advances to step S20.

In step S20, the image signals based on the first and second photoacoustic measurements which have been stored in the previous steps are read out together and comparative computation thereof is performed. In the comparative computation, the differential values of the brightness value, contrast value, signal intensity, or other image feature amounts at common two- or tree-dimensional coordinates of the image signals are calculated. The comparative computation is performed with respect to all of the coordinates, the results of the comparative computations are stored in the memory inside the signal processing unit 26, and the process advances to step S22. Such a procedure is, however, not limiting, and a variety of computations capable of reflecting the difference between the image signal based on the first photoacoustic measurement and the image signal based on the second photoacoustic measurement may be used instead of the comparative computation in step S20. For example, the image feature amount of the image signal based on the first photoacoustic measurement may be divided by the image feature amount of the image signal based on the second photoacoustic measurement. In step S22, an image signal is formed by performing image reconstruction on the basis of the differential values at all of the coordinates, and the process flow is ended. In this case, the image signal is an image signal based on the decrease in content of the contrast agent 14 inside the object 20 and, therefore, an image signal based substantially on the acoustic wave derived from the contrast agent 14. Further, this image signal is obtained by subtracting the signal component of the image signal based on the second photoacoustic measurement from the image signal based on the first photoacoustic measurement which is the image signal based on the absorber 16. Thus, this image signal is based on the acoustic wave substantially only from the absorber 12. Such a procedure is, however, not limiting, and when the temperature correction processing is not needed, the device 100 may be configured such as to omit the step of the temperature correction processing. The temperature correction processing is not needed, for example, when the temperature of the object 20 is unlikely to be raised by the irradiation with the light 30, e.g. where the device 100 is used in a cold environment, when the signal processing is wished to be increased, or when the intensity of the light 30 is comparatively small.

As a result, the image signal formed from the image signal component based on the photoacoustic wave substantially only from hemoglobin, which is the absorber 12, and the image signal formed from the image signal component based on the photoacoustic wave substantially only from the contrast agent 14 can be acquired separately from each other. Therefore, the latter image signal more accurately indicates, for example, the position inside the object 20, such as a cancer, which includes a large amount of the contrast agent 14. This is because, the brightness value of the location where the cancer is present is particularly enhanced.

Further, as a result of reducing the effect produced by the increase in temperature of the object 20, which is caused by the irradiation with the light 30, on the image signal component based on the second photoacoustic measurement, the two abovementioned image signals can be acquired with a higher accuracy.

Example 2

For example, the following process is realized when using the device 100. Thus, a sample, which is the object 20, is irradiated with the light 4 which is the pulsed laser beam from the light source 2. The piezoelectric element which is the conversion element of the probe 22 converts the acoustic wave generated from the sample under the irradiation into an analog electric signal and transmits the analog electric signal to the signal collection unit 24. The high-speed preamplifier of the signal collection unit 24 then amplifies the transmitted analog electric signal, converts it into a digital electric signal, and transmits the digital electric signal to the signal processing unit 26. A digital oscilloscope prepared for observing the state of digital electric signal inputs the transmitted digital electric signal and displays the state of the digital electric signal.

A titanium sapphire laser (LT-2211-PC, manufactured by Lotis Co.) is used as the light source 2. The wavelength of the light 4 emitted from the light source 2 is within a range of 700 nm to 1000 nm and can be variably controlled. The energy density of the light 4 is about 10 mJ/cm$^2$ to 20 mJ/cm$^2$, the pulse width (ON period of time or high-level period of time) of the light 4 is about 20 nanoseconds, and the pulse repetition frequency is 10 Hz. A non-convergence-type ultrasonic transducer (V303, manufactured by Panametrics-NDT) with a center band of 1 MHz and an element diameter of 1.27 cm is used as the piezoelectric element of the probe 22. The measuring container is a polystyrene cuvette with an optical path length of 1 mm and a sample volume of about 200 μl. The measuring container and piezoelectric element are immersed in water poured into a glass container. The distance between the measuring container and the piezoelectric element is 2.5 cm. The high-speed preamplifier in the signal collection unit 24 amplifies the signal strength of the analog electric signals from the piezoelectric element or digital electric signals based thereon. An ultrasonic preamplifier (Model 5682, manufactured by Olympus Corporation) with an amplification degree (gain) of +30 dB is used as the high-speed preamplifier.

A digital oscilloscope (DPO4104, manufactured by Tektronix Inc.) provided for the test inputs the amplified digital electric signal and displays the state of the digital electric signal on the basis of this input. The light source 2 is configured such that the polystyrene cuvette is irradiated with the pulsed laser beam 4 from the outside of the glass container. Further, a photodiode which is provided together with the digital oscilloscope for the test transmits a trigger signal to the digital oscilloscope. The digital oscilloscope inputs the trigger signal to start displaying the state of the digital electric signal on the basis of the input. The photodiode detects part of the scattered light generated by the irradiation of the polystyrene cuvette with the pulsed laser beam 4 and transmits the trigger signal on the basis of the detection. The digital oscilloscope operates in a 32-times average display mode, the number of irradiation cycles of the pulsed laser beam 4 is 32, and the digital electric signal based on the 32 cycles of irradiation is acquired. The average value of the acquired digital electric signal based on the 32 cycles of irradiation is calculated.

As a result, the state of the device 100 can be evaluated and the state of the digital electric signals acquired by the device 100 can be visualized.

Example 3

Figure 3A:
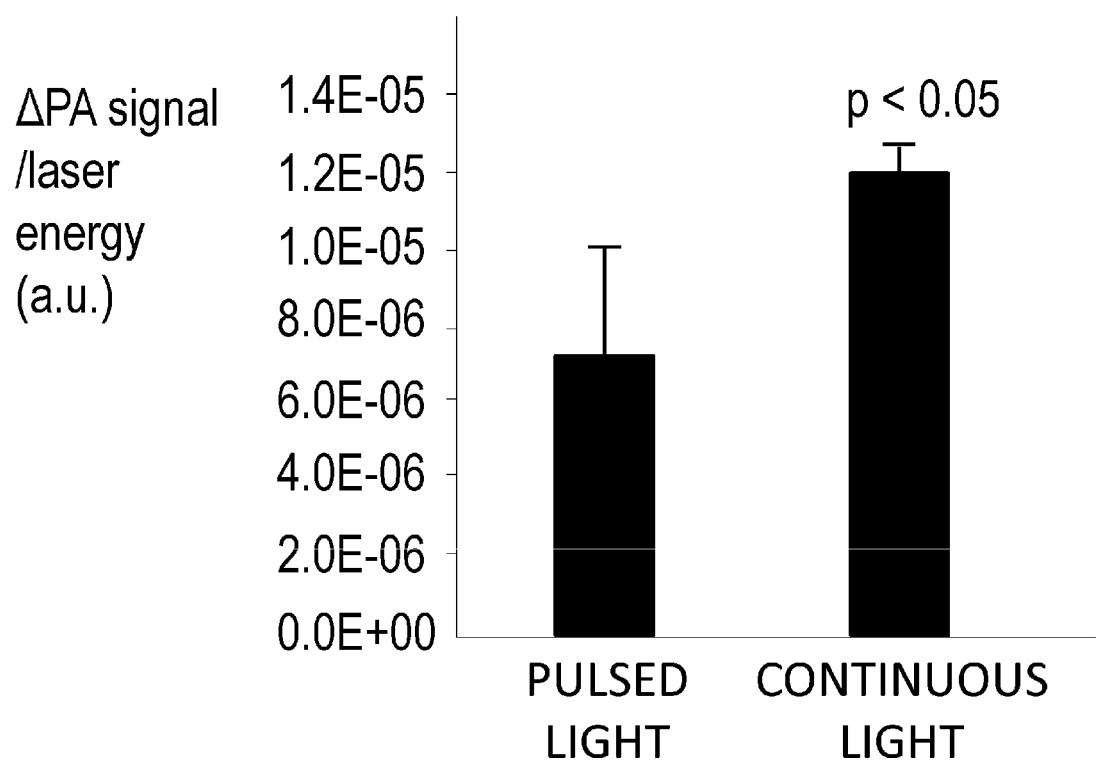
FIG. 3A illustrates the relationship between the decrease amount of the electric signal and the irradiation energy amount in Example 3.

FIG. 3A shows the reduction amount of the digital electric signal caused by bleaching in Example 3, this amount being normalized by the irradiation energy amount of the light 30. The contrast agent 14 is prepared by dissolving ICG in sterilized water such that the absorbance at the absorption maximum in the absorbance measurement with a 1 mm absorption cell is about 0.4. The contrast agent 14 is irradiated with 10 Hz pulsed light with a pulse width of about 20 nanoseconds, or LED continuous light. The operator of the device 100 measures the analog electric signals formed by conversion, with a conversion element, of the acoustic waves generated from the contrast agent 14 before and after the irradiation. The decrease in the analog electric signals caused by the irradiation is measured and normalized by the irradiation amount of the light, and the results are compared. The results presented in FIG. 3A indicate that the continuous light from the LED demonstrates a larger decrease in the digital electric signal caused by the irradiation than the pulsed light, thereby demonstrating the suitability of the continuous light for photobleaching of the contrast agent 14.

Therefore, by configuring the light source for outputting the light 30 in the device 100 from a LED capable of outputting continuous light, it is possible to enhance the photobleaching effect. As a result, the acquisition accuracy of the image signal based on the acoustic wave substantially only from the contrast agent 14 is improved and, by extension, the accuracy of the brightness value of the image signal derived from cancer, or the like, appearing therein is increased.

Example 4

Figure 3B:
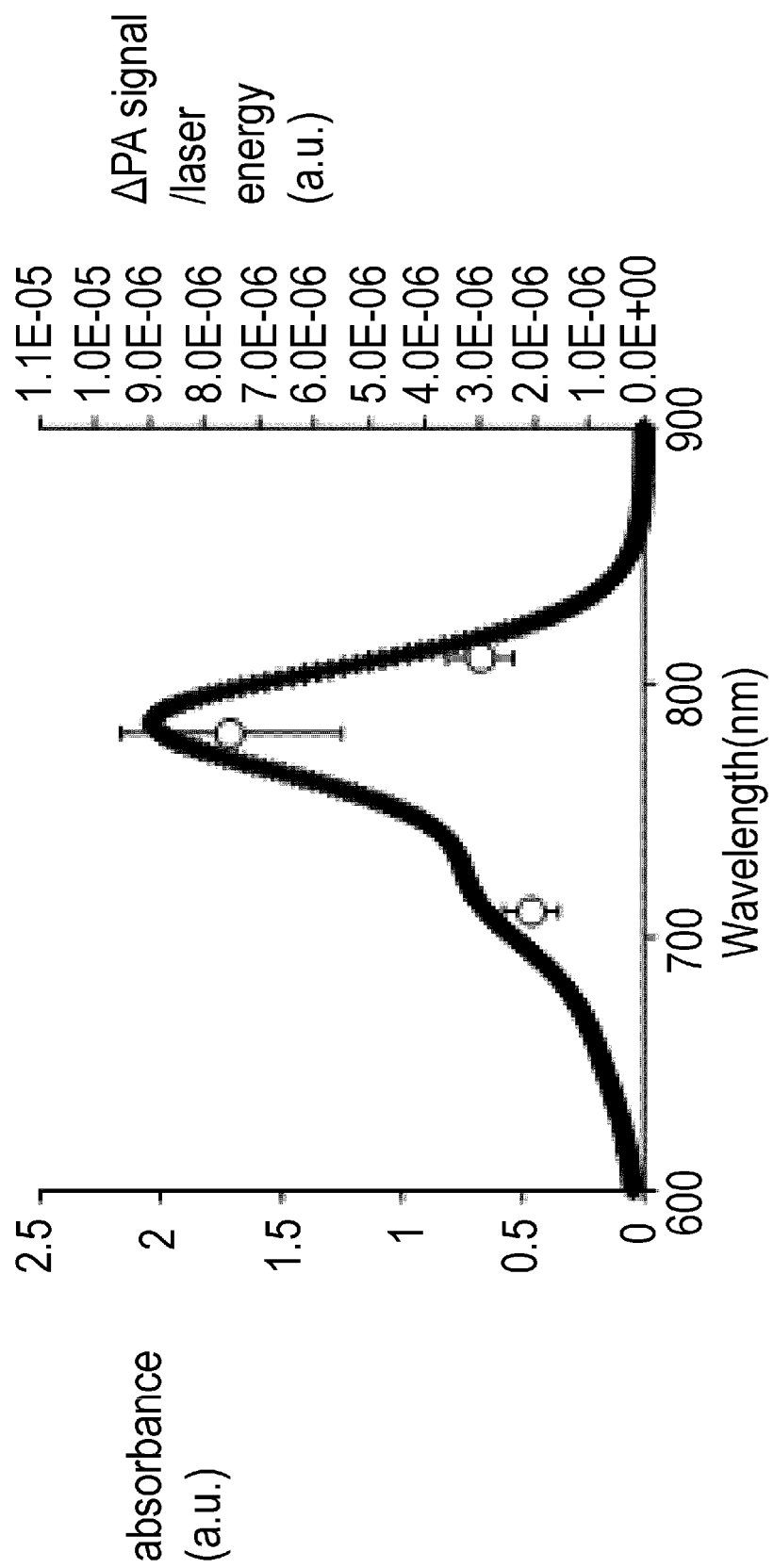
FIG. 3B illustrates the relationship between the decrease amount of the electric signal and the irradiation energy amount in Example 4.

FIG. 3B shows the reduction amount of the digital electric signal caused by bleaching in Example 4, this amount being normalized by the irradiation energy amount. The contrast agent 14 is prepared by dissolving ICG in sterilized water such that the absorbance at the absorption maximum in the absorbance measurement with a 1 mm absorption cell is about 0.4. The contrast agent 14 is irradiated with 10 Hz pulsed lights with a pulse width of about 20 nanoseconds. The wavelength of the radiated pulsed lights is 710, 780, and 810 nm. The operator of the device 100 measures the analog electric signals formed by conversion, with a conversion element, of the acoustic waves generated from the contrast agent 14 before and after the irradiation at each wavelength. The decrease in the analog electric signals caused by the irradiation at each wavelength is measured and normalized by the irradiation amount of the light, and the results are compared (see FIG. 3B). The results confirm that the ICG absorption spectrum (black line) and the decrease amount of the analog electric signal (white circles) tend to overlap. The results indicate that a light source capable of emitting a laser beam with a wavelength close to the absorption maximum of the contrast agent 14 when photobleaching the contrast agent 14 is preferred as the light source 2. The wavelength at the absorption maximum is also referred to as the absorption maximum wavelength.

Figure 3C:
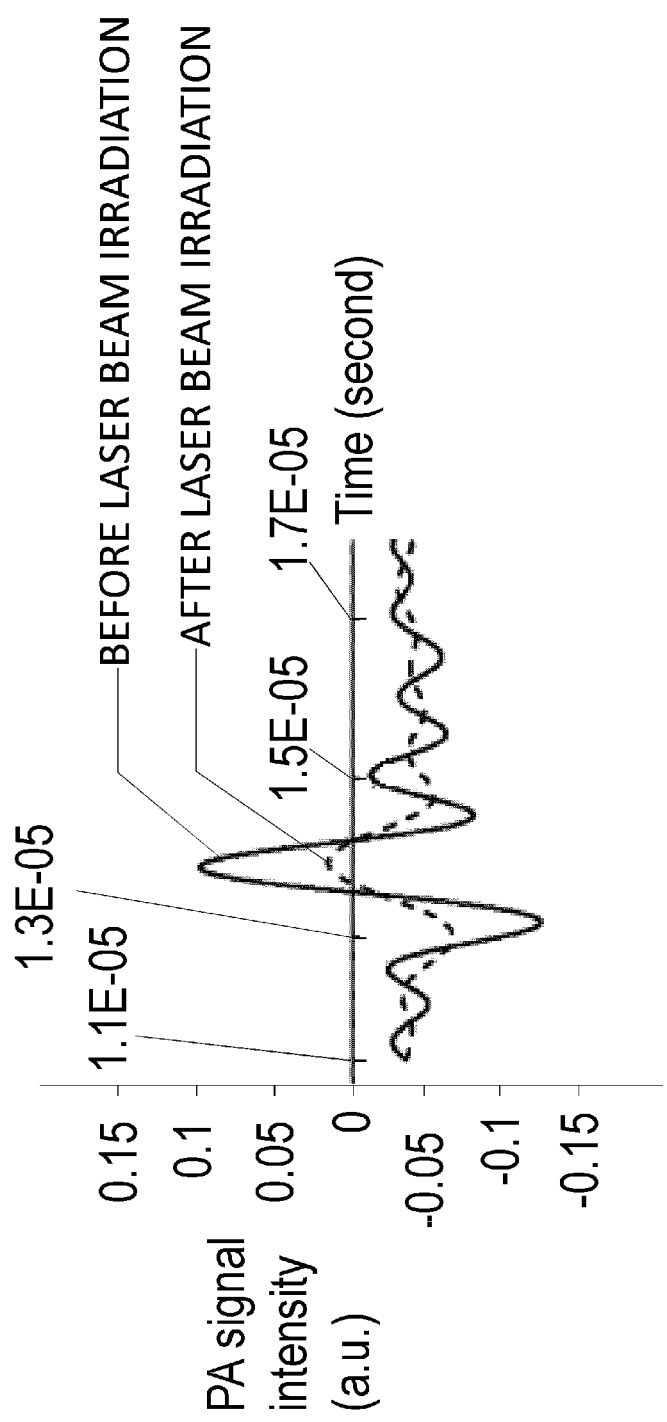
FIG. 3C illustrates the difference between the digital electric signals before and after light irradiation in Example 4.

FIG. 3C shows changes in the digital electric signal caused by the irradiation with the light 30 in Example 4. Thus, FIG. 3C shows the difference between the digital electric signals acquired by photoacoustic measurements before and after the irradiation with the light 30 when the sample of the aqueous ICG solution prepared in the above-described manner is irradiated with the pulse light for photobleaching which has a wavelength of 780 nm. The figure confirms that the irradiation with the laser beam for pohotobleaching reduces the acquired digital electric signal. In the figure, the amplitude, from the oscillation center, of the digital electric signal before the irradiation with the light 30 is larger than that after the irradiation. The same is true with respect to the analog electric signal before the conversion into the digital electric signal.

Example 5

Figure 4:
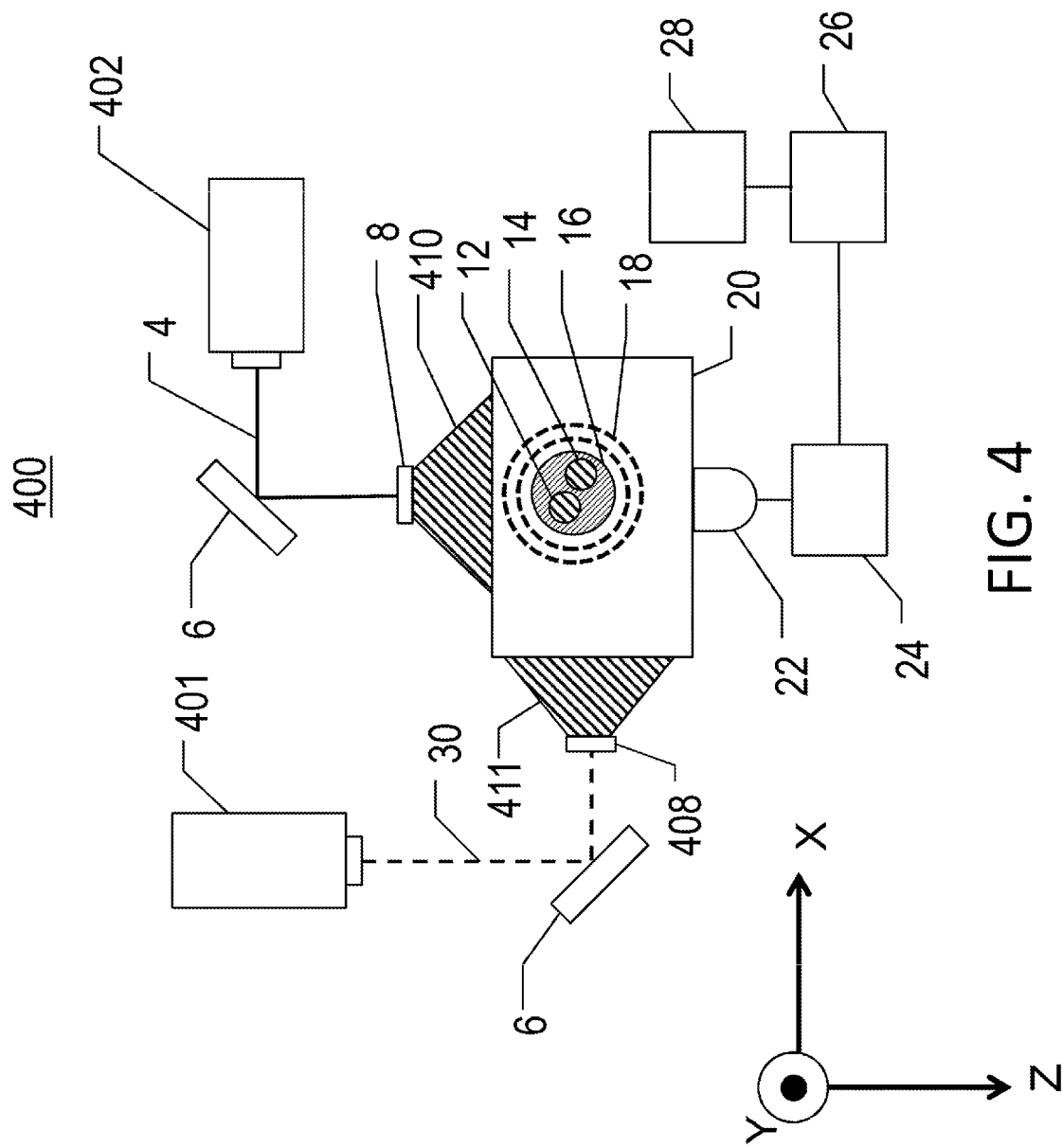
FIG. 4 is a block diagram illustrating Example 5 of the photoacoustic device of the present invention.

FIG. 4 is a block diagram illustrating Example 5 of the photoacoustic device according to the embodiment of the present invention. Components corresponding to those in FIG. 1 are assigned with same reference numerals and the explanation thereof is omitted unless otherwise needed. Further, components similar to those of Example 1 are denoted by numbers in the 400s which are the same in the tens' place and in the ones' place. The description of those components is omitted unless otherwise needed. A photoacoustic device 400 of Example 5 (referred to hereinbelow as "device 400") differs from the device 100 in that the source for generating the light 4 and the light 30 is divided into a light source 402 and a light source 401, respectively. The light source 402 emits only the light 4, and the light source 401 emits only the light 30. The irradiation of the object 20 by the irradiation unit 408 proceeds from the side surface. As a result, the object 20 is irradiated with an irradiation light 411 entirely and evenly in the thickness direction (Z direction) thereof, as compared with the irradiation with the light 30 with the device 100. Therefore, the contrast agent 14 is evenly photobleached in the depth direction of the object 20. The irradiation light 411 is formed by widening the light 30 with the irradiation unit 408 configured similarly to the irradiation unit 8. The irradiation unit 408 may also be configured to be movable in the Z-direction along the side surface of the object 20. In this case, the object 20 can be entirely and uniformly irradiated with the light 411 formed from the light 30. Further, where the irradiation unit 408, irradiation unit 410, and probe 22 are made movable, the photoacoustic measurements and photobleaching can be performed with a higher accuracy. The irradiation with the light 411 may be performed continuously or intermittently while moving the irradiation unit 408 along a circular trajectory around the object 20. The object 20 may be irradiated with the light 411 over the entire circumference. As a result, the photobleaching efficiency of the contrast agent 14 rises, and the photoacoustic measurements and photobleaching can be performed with a higher accuracy. Further, the device 400 may perform the above-described processing, while the irradiation unit 408 and the object 20 are moved relative to each other. Other features are the same as in the device 100.

Example 6

Figure 5:
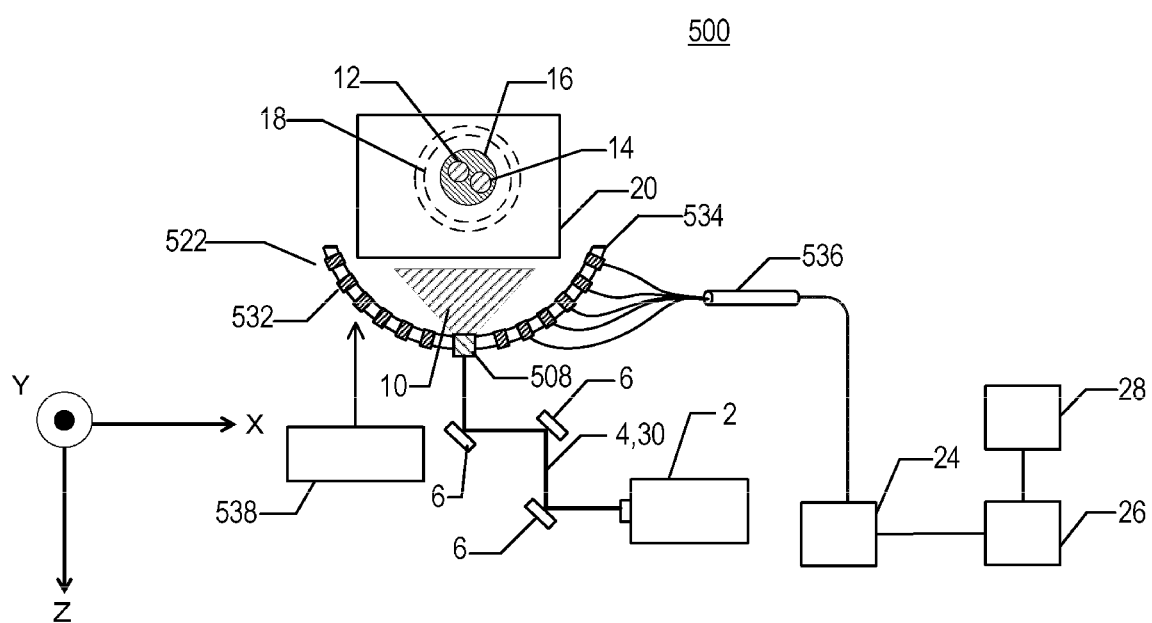
FIG. 5 is a block diagram illustrating Example 6 of the photoacoustic device of the present invention.

FIG. 5 is a block diagram illustrating Example 6 of the photoacoustic device according to the embodiment of the present invention. Components corresponding to those in FIG. 1 are assigned with same reference numerals and the explanation thereof is omitted unless otherwise needed. Further, components similar to those of Example 1 are denoted by numbers in the 500s which are the same in the tens' place and in the ones' place. The description of those components is omitted unless otherwise needed. A probe denoted by the reference numeral 522 in FIG. 5 is represented by the end surface obtained by cutting along the cutting line AA' in FIG. 6. The specific feature of a photoacoustic device 500 of the present example (referred to hereinbelow as "device 500") is in the configuration of the probe 522. The probe 522 has a plurality of conversion elements 532 and a holding member 534. The holding member 534 is formed in a substantially spherical crown shape, and holds the plurality of conversion elements 532 along the substantially spherical crown shape. The conversion elements 532 are held such as to ensure the concentration of the directions with the highest reception sensitivity. In the present embodiment, each direction with the highest reception sensitivity of the plurality of conversion elements 532 is towards the region including the center of curvature of the substantially spherical crown shape of the holding member 534. The output terminals of the conversion elements 532 for the analog electric signals are connected to respective signal wirings. The analog electric signals outputted by the conversion elements 532 are combined together by a signal line 536 configured by jointly connecting the signal wirings, and transmitted to the signal collection unit 24 through the signal line 536. Subsequent signal processing is the same as in other embodiments. Such a configuration is, however, not limiting, and the analog electric signals outputted by the conversion elements 532 may be in parallel transmitted to the signal collection unit 24 as separate individual signals, without combining the signals together by a signal line 536 configured by jointly connecting the signal wirings.

The irradiation unit 508 is configured to be integrated with the probe 522 by holding in the center of the holding member 534. The object 20 is irradiated with the light 10 from the irradiation unit 508 in the direction opposite that in Example 1. Thus, in Example 1, the irradiation unit 8 emits light in the direction towards the probe 22 (Z direction in FIG. 1), whereas in the present example, the irradiation unit 508 emits light from the probe 522 side (irradiation with the light proceeds in the −Z direction in FIG. 5). A drive device, that is, a position control unit 538, moves the probe 522. The position control unit 538 may move the probe 522, for example, spirally, and the irradiation unit 508 may emit the light 10 at an arbitrary position for light emission which is a position on a spiral trajectory along which the irradiation unit 508 moves as a result of the spiral movement thereof. The irradiation unit 508 integrated with the probe 522 may radiate the light 10 for each acoustic wave reception position (light irradiation position), following the spiral movement induced by the position control unit 538. The conversion elements 532 may receive the acoustic waves based on such irradiation, convert the received waves into analog electric signals, and transmit the signals to the signal collection unit 24. As a result, when an acoustic matching liquid is provided between the probe 522 and the object 20, the acoustic wave noise based on the vibrations of the acoustic matching liquid caused by the movement of the probe 522 can be reduced.

Figure 6:
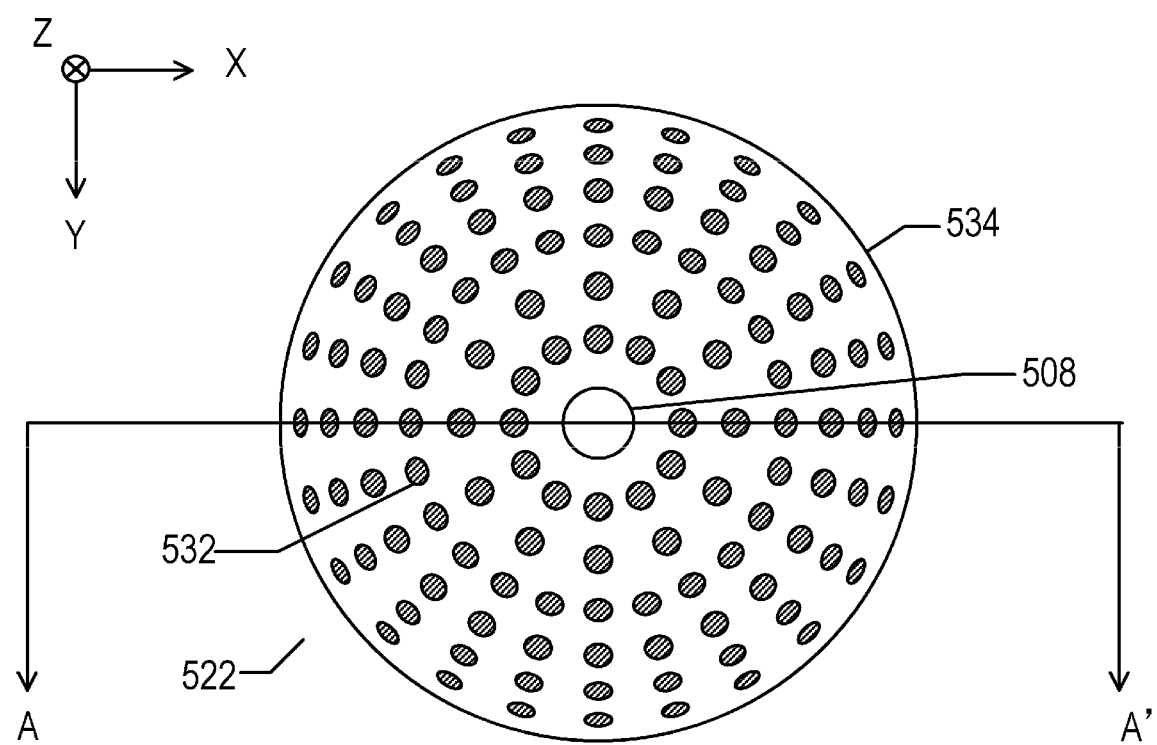
FIG. 6 is a plan view of a probe 522 and an irradiation unit 508 in Example 6 of the present invention.

FIG. 6 is a plan view of the probe 522 and the irradiation unit 508 in Example 6 of the present invention, the view being taken from the object 20 side. Components corresponding to those in FIG. 5 are assigned with the same reference numerals and the explanation thereof is herein omitted, unless otherwise needed. In FIG. 6, the probe 522 is configured by arranging the conversion elements 532 concentrically. Such a configuration is, however, not limiting, and the conversion elements 532 of the probe 522 may be arranged spirally. The irradiation unit 508 may be provided in the center of the concentric circles of the conversion elements 532. The light emission end of the irradiation unit 508 is also of a round shape, but such a configuration is not limiting, and a variety of shapes can be used. A configuration enabling the efficient reception of acoustic waves from the object 20 can thus be obtained.

Example 7

Figure 7:
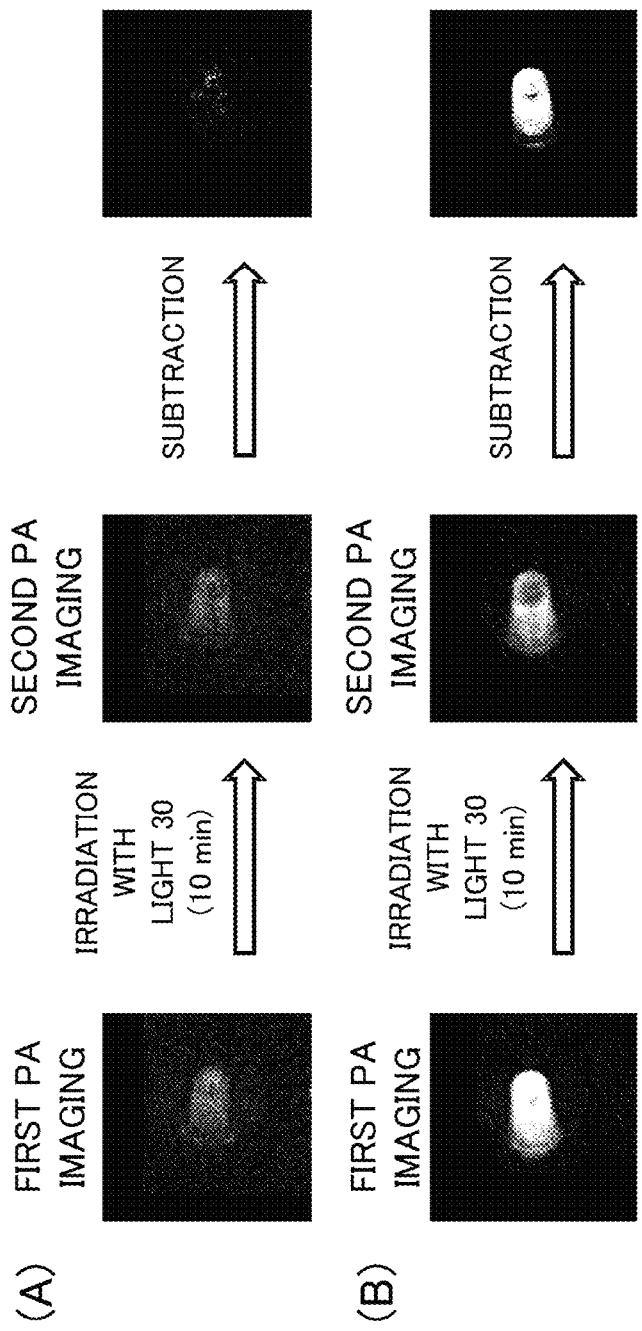
FIG. 7 illustrates a photoacoustic image and a difference image in Example 7.

FIG. 7 illustrates an image based on the first photoacoustic measurement in Example 7, an image based on the second photoacoustic measurement, and a difference image thereof. The contrast agent 14 is prepared by dissolving ICG in sterilized water to an end concentration of 1 mM. The absorber 12 is prepared by mixing blood extracted from a mouse and sterilized water at a volume ratio of 1:1. The absorber 16 is prepared by mixing blood extracted from a mouse and the contrast agent 14 at a volume ratio of 1:1. The device 100 is used which emits the 20 Hz light 4 with a pulse width of about 7 nanoseconds. The measuring container is a microtube with a capacity of 1.5 ml and a sample capacity of about 100 µl. The operator of the device 100 implements the first photoacoustic measurements of the absorber 12 and the absorber 16 to obtain a reconstructed image. The absorber 12 and the absorber 16 are then irradiated for 10 min with the light 30. Subsequently, the operator of the device 100 implements the second photoacoustic measurements of the absorber 12 and the absorber 16 to obtain a reconstructed image. Finally, the operator produces a difference image from the image based on the first photoacoustic measurement and the image based on the second photoacoustic measurement by using OsiriX Software (open source). In FIG. 7 (A), since practically no bleaching occurs in the absorber 12 (blood alone), practically no difference can be observed between the images based on the first and second photoacoustic measurements. Meanwhile, in FIG. 7 (B), in the absorber 16 (a mixture of blood and the contrast agent 14), the contrast agent 14 is bleached and, therefore, the brightness value of the difference image corresponding to the photobleaching amount of the contrast agent 14 can be observed.

Therefore, photoacoustic signals from the contrast agent 14 and the blood can be distinguished from one another even when the contrast agent 14 and the blood are mixed.

In the above-described embodiments, where the contrast agent 14 (ICG, or the like) is photobleached by irradiation with a laser beam, the absorption coefficient of the contrast agent 14 decreases. Therefore, the digital electric signal acquired by subsequent photoacoustic measurement decreases. Meanwhile, since the absorption coefficient of the absorber 12 such as hemoglobin does not change even under laser beam irradiation, the subsequently acquired digital electric signal does not change. In the photoacoustic devices of the embodiments, laser beam irradiation for photobleaching is performed between the first photoacoustic measurement and second photoacoustic measurement. Further, by obtaining the difference between the first PAT imaging information (image signal) and second PAT imaging information (image signal), it is possible to acquire data from the digital electric signals from the contrast agent 14 before and after the photobleaching, those data being based on the decrease mount of the signals. In other words, with the photoacoustic devices of the embodiments, the digital electric signal derived from the absorber 12 such as hemoglobin and the digital electric signal derived from the contrast agent 14 can be distinguished from each other. As a result, for example, a segment having a cancer, which is a segment where the contrast agent 14 is present, can be specified. For example, since a cancer requires move oxygen than a cancer-free segment, new blood vessels that are newly formed thereby take in a large amount of blood, thereby taking in a large amount of the contrast agent 14.

The implementation of various features of the present invention is not limited to the above-described embodiments. For example, the probe 522 of Example 6 may be moved in a stepwise manner, the photoacoustic devices of the embodiments may have an injection unit for holding the contrast agent 14, and the contrast agent 14 may be automatically injected from the injection unit into the object 20.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

As described hereinabove, the present invention provides a photoacoustic device that can acquire more accurate object information.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-106577, filed May 26, 2015, which is hereby incorporated by reference herein in its entirety.

REFERENCE SIGNS LIST

2: Light source, 8: Irradiation unit, 22: Probe, 26: Signal processing unit

What is claimed is:

1. A photoacoustic device comprising:
    an irradiation unit configured to generate a first acoustic wave from an object including a contrast agent by irradiating the object with a first light from a light source, and then bleach the contrast agent inside the object by irradiating the object including the contrast agent with a second light from the light source and generate a second acoustic wave from the object by irradiating the object with the first light from the light source after bleaching the contrast agent;
    a receiving unit configured to output a first electric signal upon receiving the first acoustic wave and output a second electric signal upon receiving the second acoustic wave; and
    an acquisition unit configured to acquire first property information on the object on the basis of the first electric signal, acquire second property information on the object on the basis of the second electric signal, and acquire third property information by performing differential processing on the first property information and the second property information,
    wherein the second light is pulsed light, and
    wherein a pulse interval of the second light is a period of time shorter than a triplet excited state relaxation time of the contrast agent.

2. The photoacoustic device according to claim 1, wherein the acquisition unit acquires a first image signal which indicates the first property information by forming an image signal on the basis of the first electric signal, and acquires a second image signal which indicates the second property information by forming an image signal on the basis of the second electric signal.

3. The photoacoustic device according to claim 2, wherein the acquisition unit further acquires a third image signal based on a signal component of the first image signal, this signal component originating in an acoustic wave generated from the contrast agent before the bleaching, on the basis of the first and second image signals.

4. The photoacoustic device according to claim 3, wherein the acquisition unit acquires the third image signal on the basis of a difference between the first image signal and the second image signal.

5. The photoacoustic device according to claim 4, wherein the acquisition unit acquires the third image signal by performing comparative computation on an image feature amount of the first image signal and an image feature amount of the second image signal.

6. The photoacoustic device according to claim 5, wherein the comparative computation is differential computation.

7. The photoacoustic device according to claim 1, wherein the irradiation unit induces, by irradiation with the second light, at least one of generation of reactive oxygen species and increase in temperature of a light irradiation segment in the object.

8. The photoacoustic device according to claim 1, wherein a wavelength of the second light is within a range from a wavelength which is shorter by 50 nm than a maximum absorption wavelength of the contrast agent to a wavelength which is longer by 50 nm than the maximum absorption wavelength.

9. The photoacoustic device according to claim 1, wherein the pulse interval of the second light is 0.7 milliseconds or less.

10. The photoacoustic device according to claim 1, wherein where a value of a pulse width of the second light is denoted by τ and a value of a frequency of the second light is denoted by f, the τ and f fulfil the following relationship:

$$(1-\tau \cdot f)/f < 7 \times 10^{-4}.$$

11. The photoacoustic device according to claim 1, wherein the receiving unit has a plurality of conversion elements configured to receive the first and second acoustic waves and output the first and second electric signals, respectively, and a holding member configured to hold the plurality of conversion elements and having a substantially spherical crown shape, and
the irradiation unit is integrated with the receiving unit.

12. The photoacoustic device according to claim 1, wherein the acquisition unit performs digital conversion of the first and second electric signals to generate first and second digital electric signals, respectively, and acquires the first and second property information on the basis of the first and second digital electric signals, respectively,
the phtoacoustic device further comprising a temperature correction unit configured to, when a temperature of the object rises by being irradiated with the second light, correct the second digital electric signal or the second property information on the basis of an amount of increase in temperature of the object caused by irradiation with the second light, such that the second digital electric signal or the second property information approaches a value of the second digital electric signal or the second property information obtained when the temperature of the object does not rise.

13. The photoacoustic device according to claim 12, wherein when correcting the second digital electric signal or the second property information, the temperature correction unit corrects a speed of sound and a volume expansion coefficient of the object, which have changed due to the increase in temperature of the object that is based on an energy amount of the radiated second light, such that the speed of sound and the volume expansion coefficient of the object approach a speed of sound and a volume expansion coefficient of the object obtained when the temperature of the object does not rise.

14. The photoacoustic device according to claim 1, further comprising a light source configured to generate the first light and the second light.

15. A photoacoustic device comprising:
an irradiation unit configured to generate a first acoustic wave from an object including a contrast agent by irradiating the object with a first light from a light source, and then bleach the contrast agent inside the object by irradiating the object including the contrast agent with a second light from the light source and generate a second acoustic wave from the object by irradiating the object with the first light from the light source after bleaching the contrast agent;
a receiving unit configured to output a first electric signal upon receiving the first acoustic wave and output a second electric signal upon receiving the second acoustic wave; and
an acquisition unit configured to acquire first property information on the object on the basis of the first electric signal, and acquire second property information on the object on the basis of the second electric signal,
wherein the second light is pulsed light,
wherein a pulse interval of the second light is a period of time shorter than a triplet excited state relaxation time of the contrast agent, and wherein where a value of a pulse width of the second light is denoted by τ and a value of a frequency of the second light is denoted by f, the τ and f fulfil the following relationship:

$$(1-\tau \cdot f)/f < 7 \times 10^{-4}.$$

16. A photoacoustic device comprising:
an irradiation unit configured to generate a first acoustic wave from an object including a contrast agent by irradiating the object with a first light from a light source, and then bleach the contrast agent inside the object by irradiating the object including the contrast agent with a second light from the light source and generate a second acoustic wave from the object by irradiating the object with the first light from the light source after bleaching the contrast agent;
a receiving unit configured to output a first electric signal upon receiving the first acoustic wave and output a second electric signal upon receiving the second acoustic wave; and
an acquisition unit configured to acquire first property information on the object on the basis of the first electric signal, and acquire second property information on the object on the basis of the second electric signal,
wherein the receiving unit has a plurality of conversion elements configured to receive the first and second acoustic waves and output the first and second electric signals, respectively, and a holding member configured to hold the plurality of conversion elements and having a substantially spherical crown shape, and
wherein the irradiation unit is integrated with the receiving unit.

17. A photoacoustic device comprising:
an irradiation unit configured to generate a first acoustic wave from an object including a contrast agent by irradiating the object with a first light from a light source, and then decrease an absorption coefficient of the contrast agent inside the object at wavelength of the first light by irradiating the object including the contrast agent with second light and generate a second acoustic wave from the object by irradiating the object with the first light from the light source after decreasing the absorption coefficient of the contrast agent;
a receiving unit configured to output a first electric signal upon receiving the first acoustic wave and output a second electric signal upon receiving the second acoustic wave; and
an acquisition unit configured to acquire first property information on the object on the basis of the first electric signal, and acquire second property information on the object on the basis of the second electric signal,
wherein the second light is pulsed light, and
wherein a pulse interval of the second light is a period of time shorter than a triplet excited state relaxation time of the contrast agent.

18. The photoacoustic device according to claim 17, wherein both the first light and the second light are emitted from a light source.

19. The photoacoustic device according to claim 18, further comprising the light source configured to generate the first light and the second light.

20. The photoacoustic device according to claim 17, wherein the pulse interval of the second light is 0.7 milliseconds or less.

21. The photoacoustic device according to claim 17, wherein, where a value of a pulse width of the second light is denoted by $\tau$ and a value of a frequency of the second light is denoted by f, the $\tau$ and f fulfil the following relationship:

$$(1 - \tau \cdot f)/f < 7 \times 10^{-4}.$$

22. The photoacoustic device according to claim 17, wherein the acquisition unit is configured to acquire third property information by performing differential processing on the first property information and the second property information.

\* \* \* \* \*